United States Patent [19]

Kato

[11] Patent Number: 4,686,857

[45] Date of Patent: Aug. 18, 1987

[54] METHOD AND APPARATUS FOR EVALUATING THE PERFORMANCE OF DIELECTRIC SUBSTANCES

[75] Inventor: Takayuki Kato, Aichi, Japan

[73] Assignee: Kabushiki Kaisha Toyota Chuo Kenkyusho, Aichi, Japan

[21] Appl. No.: 585,257

[22] Filed: Mar. 1, 1984

[30] Foreign Application Priority Data

| Mar. 4, 1983 | [JP] | Japan | 58-36384 |
| Mar. 7, 1983 | [JP] | Japan | 58-37210 |
| Mar. 14, 1983 | [JP] | Japan | 58-42978 |
| Mar. 14, 1983 | [JP] | Japan | 58-42979 |
| Mar. 14, 1983 | [JP] | Japan | 58-42980 |
| Apr. 8, 1983 | [JP] | Japan | 58-62691 |
| Jul. 4, 1983 | [JP] | Japan | 58-121411 |

[51] Int. Cl.$^4$ .................. G01F 23/26; G01R 27/26
[52] U.S. Cl. ........................ 73/304 R; 73/304 C; 324/60 CD; 324/61 R; 374/145
[58] Field of Search ............ 73/304 C, 64, 10, 61.1 R, 73/61 R, 304 R; 324/61 R, 61 P, 60 CD; 361/280, 284; 307/308; 374/165

[56] References Cited

U.S. PATENT DOCUMENTS

| 1,960,168 | 5/1934 | Schoenberg | 324/61 R |
| 2,455,543 | 12/1948 | Williams | 324/60 CD X |
| 3,067,385 | 12/1962 | Rykoskey | 324/61 P |
| 3,580,074 | 5/1971 | Wescott | 73/304 C |
| 3,879,657 | 4/1975 | Nystuen et al. | 324/442 X |
| 3,901,079 | 8/1975 | Vogel | 73/304 C |
| 4,007,629 | 2/1977 | Hochstein | 73/53 |
| 4,065,715 | 12/1977 | Jaffe et al. | 324/60 CD |
| 4,340,938 | 7/1982 | Rosso | 73/61.1 R |
| 4,389,889 | 6/1983 | Larson | 73/304 C |
| 4,450,501 | 5/1984 | Kobayashi | 73/304 C |
| 4,458,524 | 7/1984 | Meador et al. | 374/101 X |
| 4,470,008 | 9/1984 | Kato | 73/304 C |
| 4,471,295 | 9/1984 | Vermeiren | 324/61 R |
| 4,472,968 | 9/1984 | Coates | 73/304 C |

FOREIGN PATENT DOCUMENTS

| 1034861 | 7/1966 | United Kingdom . |
| 1292332 | 10/1972 | United Kingdom . |
| 1418918 | 12/1975 | United Kingdom . |

Primary Examiner—Daniel M. Yasich
Attorney, Agent, or Firm—Oblon, Fisher, Spivak, McClelland, & Maier

[57] ABSTRACT

An apparatus for evaluating the performance of a dielectric substance includes: at least a pair of electrodes disposed in contact with the dielectric substance to be measured; a power supply for applying a pulse voltage to the electrodes; a current detector for detecting a transient response current flowing between the electrodes dependent on the component of the dielectric substance disposed between the electrodes; and a signal processor for evaluating the performance of the dielectric substance. The performance evaluation may be performed based on at least one of a peak value of the transient response current at a certain period of time, a difference between the peak value and a value at a fixed period of time after the peak value, and a ratio of the peak value to the difference between the two values. With this method and apparatus, the performance of the dielectric substance can quantitatively be evaluated.

42 Claims, 59 Drawing Figures

FIG. 1
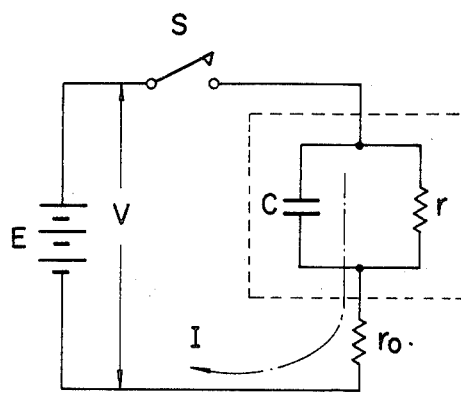
FIG. 2A
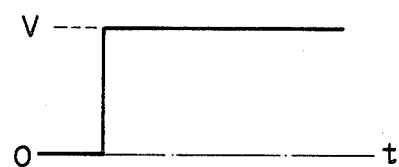
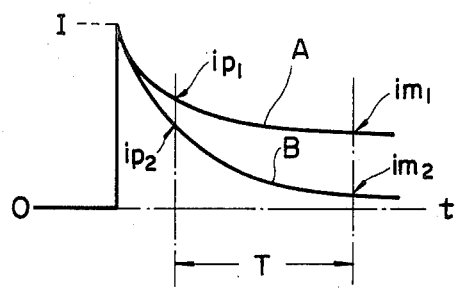
FIG. 2B

F I G. 3(a)
NEW OIL
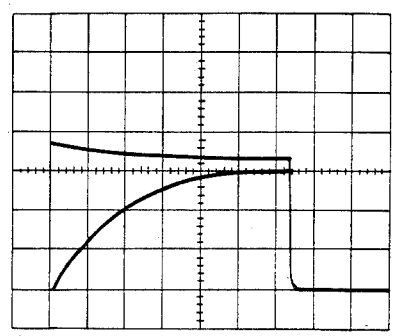
F I G. 3(b)
USED OIL
8,000 Km
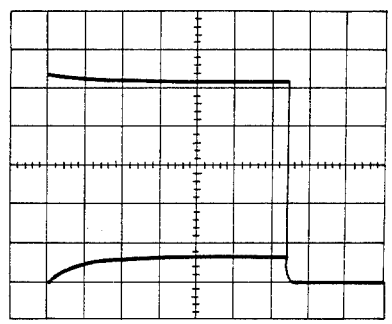
F I G. 3(c)
USED OIL
17,000 Km
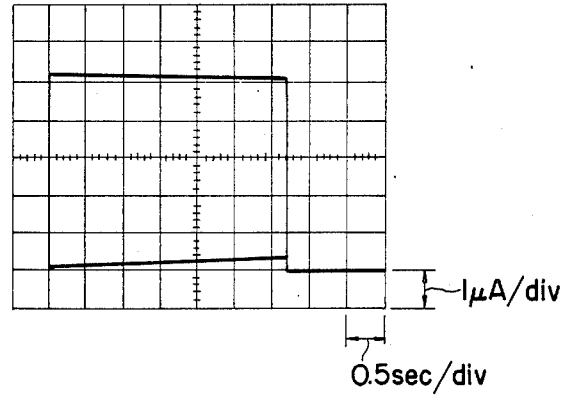
1μA/div
0.5sec/div

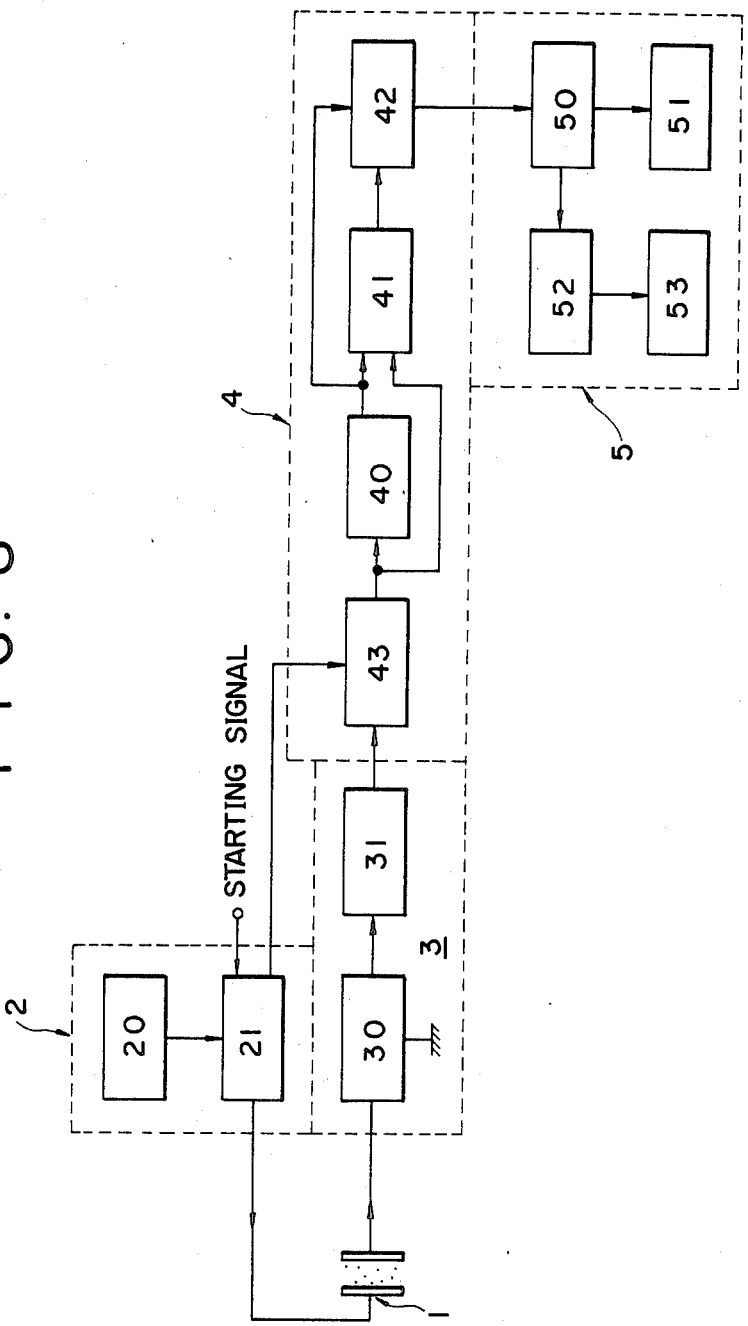

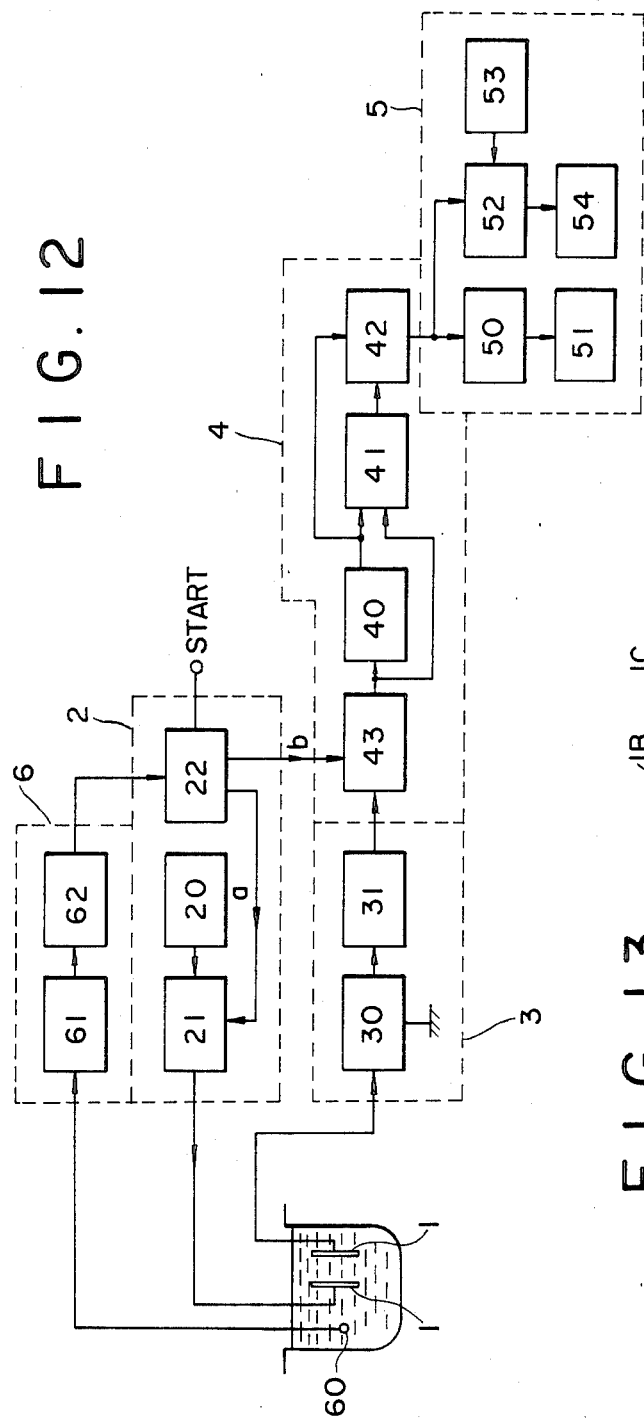

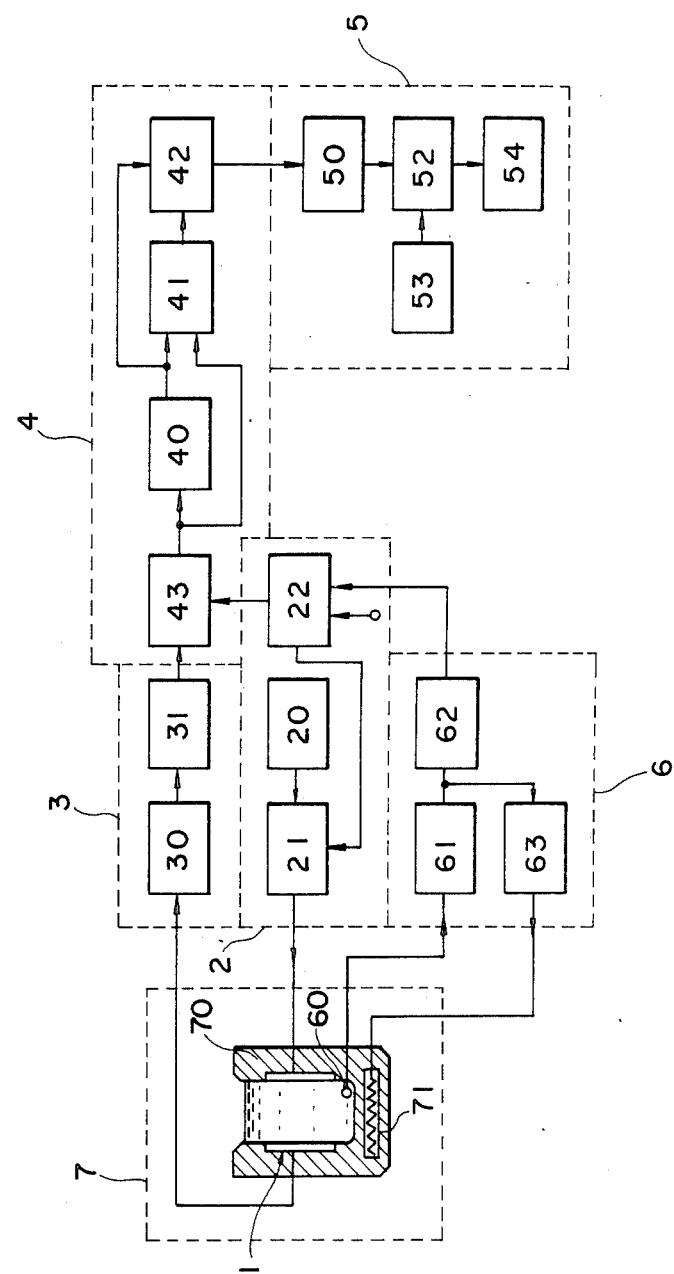

NEW OIL $ip = 5.1$
$ip/\Delta i = 1.45$
$1\mu A/div$
$0.5 sec/div$

NEW OIL $ip = 2.9$
$ip/\Delta i \doteqdot 1.45$

USED OIL   17,000 Km $ip = 6.1$
$ip/\Delta i = 15$

USED OIL   17,000 Km $ip = 3.3$
$ip/\Delta i = 12.8$

Pd

1μA/div 0.5sec/div

Cu

CuZn

STAINLESS STEEL

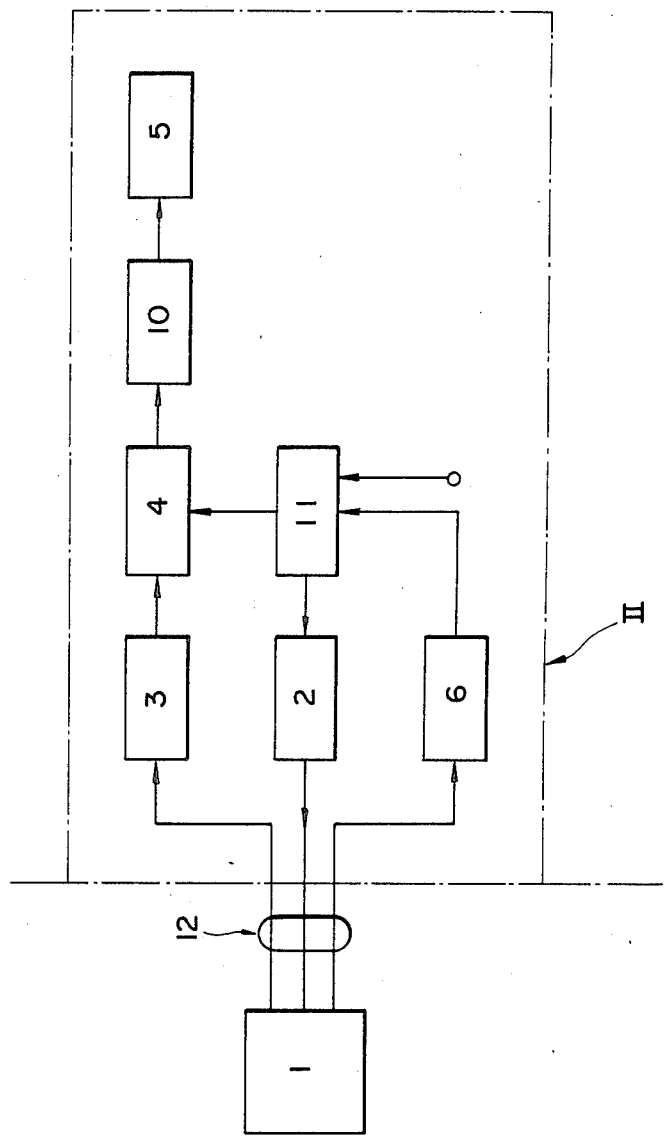

FIG. 34(a) P₁
FIG. 34(b) P₂
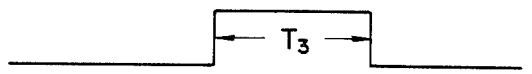
FIG. 34(c) P₃
FIG. 34(d) P₄
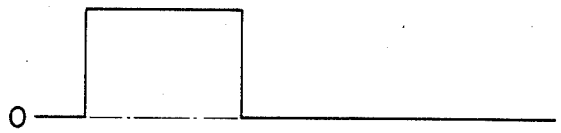
FIG. 34(e) V
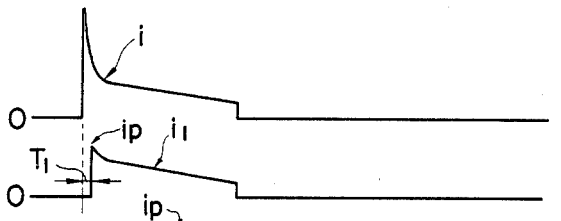
FIG. 34(f) i
FIG. 34(g) i₁
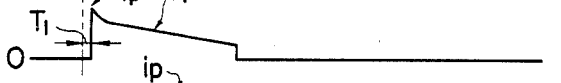
FIG. 34(h) ip
FIG. 34(i) Δi
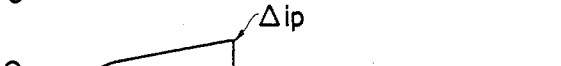
FIG. 34(j) Δip
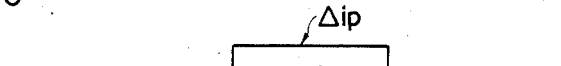
FIG. 34(k) ip₁
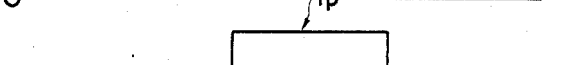
FIG. 34(l) ip/Δip

METHOD AND APPARATUS FOR EVALUATING THE PERFORMANCE OF DIELECTRIC SUBSTANCES

BACKGROUND OF THE INVENTION

1. Field of the invention:

The present invention relates to a method of and an apparatus for evaluating the performance of a dielectric fluidic substance such as lubricating oil, cutting oil, coolant oil, and the like.

2. Description of the Prior Art:

Generally, dielectric substances such as oil and grease gradually vary in performance in its process of use or with time. Lubricating oil, as an example of such a substance, is employed as a lubricant for mechanical frictional members in engines, in automobiles and ships and industrial machines such as machine tools and textile machines. The lubricating performance of the lubricating oil gradually decreases due to entrapment of metal particulates in the oil in the process of use or oxidization and property changes of the oil itself.

The lubricating oil used in internal combustion engines particularly suffers from a large reduction of performance as it is used. Therefore, it is necessary to periodically inspect the lubricating oil and replace it, if its performance is lowered, with new lubricating oil for maintaining required characteristics of the internal combustion engine.

Several processes have been employed for recognizing or grasping deterioration of lubricating oil. One known such process is a quantative analysis of a viscosity reduction, an oxidation degree, an increase of residual carbon, an increase of insolubles, and the like. Another conventional process is electrically effected for measuring the above variables as variations in the dielectric constant or conductivity.

For the quantative analysis of the variables, it is necessary to sample the lubricating oil from an internal combustion engine and subject the oil to a chemical analysis. This procedure is quite time-consuming, requires expensive and complex measuring equipment, and hence is not practical.

The method of recognizing the performance of lubricating oil based on a variation in its dielectric constant and conductivity is relatively simple. However, the oil performance cannot accurately be determined simply on the basis of the sole information of dielectric constant or conductivity.

More specifically, lubricating oils for use in internal combustion engines vary in initial performance dependent on the kinds of additives contained therein, and their dielectric constants and conductivities differ widely. The manner in which the oil performance is lowered varies with the condition in which the engine operates. Therefore, the latter method is disadvantageous in that the dielectric constant or conductivity as measured may not be a direct indication of the performance of the lubricating oil itself.

Still another evaluation process which has conventionally been carried out in general for lubricating oils for automobiles is an organoleptic test which is normally conducted by checking the running distance of an automobile or inspecting the color of the oil or its feel (through examination of the viscosity and insolubles on finger tips). The organoleptic examination however is not related to the oil performance and not a sensible method to resort to. This method does not allow the essential performance of lubricating oil to be recognized, and oil replacement is indicated only by indirect information such as the running distance or oil contamination. Therefore, the organoleptic method sometimes results in a wasteful consumption of lubricating oil, and is disadvantageous from the standpoint of saving resources.

SUMMARY OF THE INVENTION

The present invention has been made in an effort to eliminate the foregoing shortcomings with the prior method and apparatus for evaluating the performance of dielectric substances.

It is an object of the present invention to provide a method of and an apparatus for evaluating the performance of a dielectric substance such as lubricating oil, cutting oil, or the like, directly, simply, accurately, and highly reliably to determine the degree of contamination and service life of the substance, thus contributing to saving of resources such as lubricating oil.

Another object of the present invention is to provide a method of and an apparatus for easily and accurately evaluating the performance, type and quality of a dielectric substance based on the transient response charateristics of the substance.

Still another object of the present invention is to provide an apparatus for evaluating the performance of a dielectric substance applicable to an automobile for notifying the driver of the performance condition of lubricationg oil, and also to a machining tool or the like for notifying the operator of the performance condition of working oil, cutting oil or quenching oil.

A further object of the present invention is to provide an apparatus for evaluating the performance of a dielectric fluidic substance for use at automobile repair shops or service stations to measure the performance, contamination and service life of lubricating oil.

A method of evaluating the performance of a dielectric fluidic substance according to the present invention comprises the steps of applying a pulse voltage to at least a pair of electrodes arranged in contact with the dielectric fluidic substance to be measured, detecting a transient response current flowing between the electrodes dependent on the component of the dielectric fluidic substance disposed between the electrodes, and evaluating the performance of the dielectric fluidic substance based on the detected current.

An apparatus for evaluating the performance of a dielectric fluidic substance according to the present invention comprises at least a pair of electrodes disposed in contact with the dielectric fluidic substance to be measured, a power supply means for applying a pulse voltage to the electrodes, a current detecting means for detecting a current flowing between the electrodes dependent on the component of the dielectric fluidic substance disposed between the elecrodes, and a signal processing means for evaluating the performance of the dielectric fluidic substance based on the detected current.

According to the method and apparatus of the invention, the performance of the dielectric fluidic substance can quantatively be evaluated with a simple arrangement.

According to a first aspect of the present invention, the measured variation in the current flowing through the dielectric fluidic substance is displayed in relation to the performance of the dielectric fluidic substance. According to this aspect, the performance of the dielectric fluidic substance can quantitatively be evaluated with utmost ease, and the condition of the performance can easily be confirmed.

According to a second aspect of the present invention, the performance of the dielectric fluidic substance is evaluated by comparing the measured variation in the current flowing through dielectric substance with a reference value established in advance. According to this aspect, the condition of the performance of the dielectric substance can be determined on the basis of a proper evaluation reference, and the performance of the dielectric fluidic substance can be evaluated with high accuracy.

According to a third aspect of the invention, the temperature of the substance is also detected, and the pulse voltage is applied to the electrodes when the temperature is at a prescribed temperature. According to this aspect, the temperature of the dielectric fluidic substance can be grasped, and the performance evaluation can properly and stably be performed.

According to a fourth aspect of the present invention, the temperature of the dielectric fluidic substance is controlled so that the temperature is at a prescribed value. According to this aspect, the temperature of the dielectric fluidic substance can be established as desired so that the maximum evaluation sensitivity can be obtained.

According to a fifth aspect of the invention, the evaluation is performed by measuring the performance and liquid level of the dielectric fluidic substance on the basis of a variation of the current measured. According to this aspect, two different property values, i.e., the performance and liquid level of the substance, can be evaluated by a single electrode assembly composed of at least a pair of electrodes.

According to a sixth aspect of the invention, the performance evaluation is performed based on at least one of a peak value of the transient response current at a certain period of time, a difference between the peak value and a value at a fixed period of time after the peak value, and a ratio of the peak value to the difference between the two values. In this aspect, the evaluation with high accuracy and high quality is possible.

According to a seventh aspect of the present invention, at least one of the electrodes is made of a material having high activity to the dielectric fluidic substance. This allows charged particles in the dielectric fluidic substance to react with the electrode with high sensitivity, thus ensuring high accuracy and high quality in evaluation.

The above and other objects, features and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 1 is a fundamental circuit diagram showing the principles of evaluation of the performance of a dielectric fluidic substance according to the present invention;

FIG. 2 is a set of diagrams illustrative of the principles of evaluation of the performance of a dielectric fluidic substance according to the present invention;

FIGS. 3(a) through 3(c) are representations of the results of measurement according to the present invention;

FIGS. 8 through 10 illustrate a fifth embodiment of the invention, FIG. 8 being a block diagram, FIG. 9 a set of waveform diagrams illustrative of current variations, and FIG. 10 a diagram showing the results of measurement according to the fifth embodiment;

: FIG. 12 is a block diagram showing a seventh embodiment of the invention;

FIG. 13 is a perspective view of an electrode assembly for use in an eighth embodiment;

FIG. 14 is a block diagram of a ninth embodiment;

FIGS. 31 through 34(a-l) are illustrative of an apparatus for warning engine oil deterioration of a twenty-second embodiment, FIG. 31 being a block diagram of the apparatus, FIG. 32(a) a side elevational view of a portion including a sensor means, FIG. 32(b) a cross-sectional view of the sensor means, FIG. 32(c) a side elevational view of an electrode in the sensor means, FIG. 33 a block diagram of the apparatus, and FIGS. 34a-34l waveform diagrams showing current variations.

DETAILED DESCRIPTION

Figure 4:
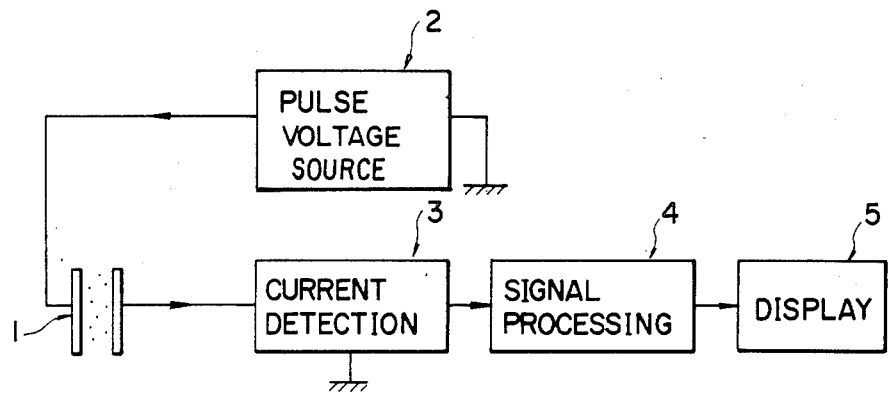
FIGS. 4 through 7 are block diagrams showing first to fourth embodiments of the present invention.

The basic principles in a method of and an apparatus for evaluating the performance of a dielectric substance according to the present invention will be described with reference to FIGS. 1 through 3.

A dielectric substance contacting a pair of electrodes is indicated by an equivalent circuit shown in FIG. 1, and represented by an internal resistance r and a capacitance C with a dielectric constant $\epsilon_s$. When a stepped voltage V as shown in FIG. 2 is applied by a power supply E through a switch S, a transient response current expressed by the following equation flows through the equivalent circuit:

$$I \approx \frac{V}{r_0} \exp\left(-\frac{t}{r_0 C}\right) + \frac{V}{r}$$

The current I will be described in detail with reference to the current waveform shown in FIG. 2.

Immediately after the voltage V is applied to the pair of electrodes, a transient current expressed by $V/r_0$ flows due to the circuit resistance $r_0$. As time goes on, the current decreases exponentially. Then, a steady-state current $V/r$ which exhibits a gradual variation flows due to the resistance r of the dielectric fluidic substance at the time the pulse voltage is imposed on the dielectric fluidic substance. The resistance r and the capacitance C are variables dependent on the dielectric fluidic substance, and vary largely dependent on the type and property of the substance. For example, the curve A of the transient response current I flows when the resistance r is small and the capacitance C is large, and the curve B flows when the resistance r is large and the capacitance C is small. Assuming that an initial value of the transient response current in a fixed period of time in the curve A is expressed by $ip_1$ a current upon elapse of a fixed period of time is expressed by $im_1$, the current $ip_1$ depends on the resistance r of the dielectric constant, that is, a propery proportional to the conductivity, and a variation in the current I, that is, $ip_1 - im_1$, dependent on a property proportional to a variation in the conductivity of the dielectric fluidic substance. Where the current $ip_1$ is large, a large quantity of mixed material such as metal particulates and residual carbon is present in the dielectric fluidic substance, resulting in a high conductivity and a small electric resistance. Where $ip_1 - im_1$ (hereinafter referred to as a difference $\Delta i$) is small, a variation of the conductivity of the dielectric substance is also small.

The curves A and B of the transient response current characteristics shown in FIG. 2 are compared as follows:

$ip_1 > ip_2$ $ip_1 - im_1 < ip_2 - im_2$

Accordingly, the dielectric fluidic substance having the curve A has a greater conductivity and a smaller conductivity variation than those of the dielectric fluidic substance having the curve B.

Transient response currents were measured as shown in FIGS. 3(a) through 3(c) with respect to engine oils which are typical lubricating oils. In FIGS. 3(a) through 3(c), the ordinate shows current and the abscissa shows time. FIG. 3(a) shows current characteristics of a new oil, FIG. 3(b) those of an oil used in an automobile after running over 8,000 km, and FIG. 3(c) those of an oil used in an automobile after running over 17,000 km. The current characteristics indiciate transient response currents in a fixed time T shown in FIG. 2. In FIGS. 3(a) through 3(c), an initial value of an upper waveform represents ip while a final value of a lower waveform represents $\Delta i$. The values ip, ip $-$ im or $\Delta i$ obtained from the current waveforms shown are indicated in a table 1 (the values ip and $\Delta i$ in the table 1 show indicated values on the waveforms of the current characteristics shown in FIGS. 3(a) through 3 (c).

TABLE 1

|  | New oil | 8,000 km | 17,000 km |
|---|---|---|---|
| ip | 3.7 | 5.3 | 5.3 |
| $\Delta i$ | 3 | 0.7 | 0.2 |
| ip/$\Delta i$ | 1.23 | 7.57 | 26.5 |

It will be understood that ip increases in proportion to the running distance, and $\Delta i$ decreases in proportion to the running distance. The increase of ip appears to be caused by the fact that the lubricating oil such as engine oil has metal particulates and residual carbon increasingly contained therein during its process of use, resulting in a progressively higher conductivity. The decrease of $\Delta i$ appears to be caused by the fact that the variation in the conductivity of engine oil becomes gradually smaller under the influence of water content and insolubles.

More specifically, a peak current value ip of the transient response current at a certain period of time through the dielectric substance depends on a property proportional to the conductivity of the dielectric fluidic substance. For lubricating oil, for example, the peak current value depends on the quantity of charged particles produced upon dissociation or electrolytic dissociation of molecules of various foreign matter mixed in the oil, such as metal particulate, residual carbon, and insolubles, and an additive incorporated for improving the performance of the lubricating oil. Accordingly, an increase of ip is indicative of the degree to which the performance of lubricating oil is lowered. Comparison of current values ip of a plurality of dielectric fluidic substances can determine the types and properties of such dielectric fluidic substances.

A variation in current $\Delta i$ within a fixed period of time after the peak current value ip at a desired position of the transient response current in a dielectric fluidic substance is depedent on a property proportional to a variation of the conductivity of the dielectric fluidic substance. For lubricating oil such as engine oil, for example, molecules as of metal particulate, water, and insolubles mixed into the oil during its process of use are associated into large colloidal particles, and hence charged particles generated upon dissociation or electrolytic dissociation of the colloidal particles are prevented from freely moving through the lubricating oil. As a result, the variation of the conductivity of the lubricating oil itself is virtually reduced, and so is the current variation $\Delta i$.

Any reduction of $\Delta i$ is indicative of the presence of large colloidal particles due to entrapment of foreign matter, and represents the degree to which the performance of lubricating oil is lowered. Comparison of current variations $\Delta i$ of a plurality of dielectric fluidic substances can determine the types and properties of such dielectric fluidic substances.

For lubricating oil such as engine oil, therefore, the greater the current value ip and the smaller the current variation $\Delta i$, the lower the perfomance of the lubricating oil.

The current value ip dependent on the conductivity of the dielectric fluidic substance was divided by the current variation Δi dependent on the variation of the conductivity for different oils, and the ratios are shown in the table 1. Since the ratio increases in proportion to the period in which the oil is used (running distance), the ratio is an effective means for evaluating the performance of a dielectric fluidic substance such as engine oil.

Based on the foregoing basic principles and various experimental studies and facts, the essential performance of a dielectric fluidic substance such an lubricating oil can be evaluated directly, accurately, reliably and simply by placing the dielectric fluidic substance in contacting relation to a pair of electrodes, applying a pulse voltage to the electrodes, and measuring a peak value of a transient response current flowing between the electrodes, a variation in the current in a fixed period of time, or a ratio of the peak value to the current variation, while the pulse voltage is being applied to the electrodes.

Specific embodiments of a method of and an apparatus for evaluating the performance of a dielectric fluidic substance according to the present invention will hereinafter be described.

FIG. 4 shows a method of evaluating the performance of a dielectric fluidic substance according to a first embodiment of the present invention. According to this method, a pulse voltage is applied by a power supply means to at least a pair of electrodes placed in contacting relation to a dielectric substance to be measured, and a transient response current flowing between the electrodes dependent on the component of the dielectric fluidic substance disposed between the electrodes is measured to evaluate the performance of the dielectric substance based on the measured current.

An apparatus according to this embodiment comprises at least a pair of electrodes 1 placed in contacting relation to a dielectric fluidic substance to be measured, a voltage source 2 for applying a pulse voltage to the electrodes, a current detecting means 3 for detecting transient response current flowing through the dielectric fluidic substance when the pulse voltage is applied to the electrodes 1, a signal processing means 4 responsive to an output from the current detecting means 3 for analyzing characteristics of the transient response current, and a display means 5 responsive to an output from the signal processing means 4 for displaying the performance value of the dielectric fluidic substance.

With the method and apparatus thus arranged according to the first embodiment, when the pulse voltage is applied by the voltage source 2 to the electrodes 1 contacting the dielectric fluidic substance, the dielectric fluidic substance disposed between the electrodes 1 is charged and a current flows through the dielectric fluidic substance. The current has different transient responses dependent on the properties (conductivity, its variation and the like) of the dielectric fluidic substance. The current is detected by the current detecting means 3, and its transient response is analyzed by the signal processing means 4. The signal processing means 4 measures a transient response current of the current, that is, a peak value of the current, a variation in the current in a fixed period of time while the pulse voltage is being applied, and a ratio of the peak value to the current variation. The results are displayed on the display means 5 according to indices indicative of the performance of the dielectric fluidic substance. The evaluation of the performance of the dielectric fluidic substance, particularly lubricating oil for automobiles, can be expressed by the degree of contamination and service life thereof. The performance can also be displayed according to the type of lubricating oil and the extent to which the property of oil has changed with time.

The apparatus for evaluating the performance of a dielectric substance based on the foregoing principle and arrangement is of quite simple in construction, capable of accurately detecting the performance of dielectric fluidic substances, and hence has many industrial advantages.

The voltage source 2 may generate a pulse voltage or a stepped voltage provided it will cause a transient response from the dielectric fluidic substance.

The current detecting means 3 may detect any signal proportional to a transient response current flowing through a dielectric fluidic substance, one example being a voltage drop in the voltage source 2.

Figure 5:
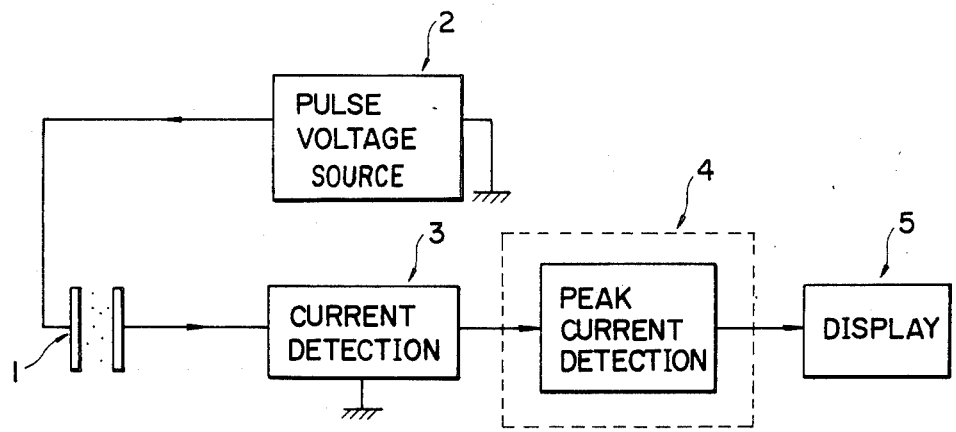

FIG. 5 illustrates a method of and an apparatus for evaluating the performance of a dielectric fluidic substance according to a second embodiment (belonging to the first aspect). Identical parts shown in FIG. 5 are denoted by identical reference characters in FIG. 4, and will not be described in detail.

According to the method of the second embodiment, the measurement of a current variation with the processing means 4 is carried out by detecting a peak current value at a desired position of a current flowing between the electrodes due to a transient response from the dielectric fluidic substance. The apparatus according to the second embodiment comprises a pair of electrodes 1 placed in contacting relation to a dielectric fluidic substance to be measured, a voltage source 2 for applying a pulse voltage to the electrodes, a current detecting means 3 for detecting a transient response current flowing through the dielectric substance when the pulse voltage is applied to the electrodes 1, a processing circuit means 4 composed of a peak detecting means 40 for detecting a peak value at a desired position of the transient response current detected by the current detecting means 3, and a display means 5 for displaying an output from the peak detecting means 40 as the performance value of the dielectric fluidic substance.

With the method and apparatus thus arranged according to the second embodiment, when a pulse voltage is applied to the dielectric fluidic substance contacting the pair of electrodes 1, the peak value at a desired position (upon elapse of a desired period of time after the pulse voltage has been applied) of the current due to a transient response of the dielectric fluidic substance is dependent on the conductivity of the dielectric fluidic substance. The performance of the dielectric fluidic substance such as lubricating oil for automobiles can be grasped by determining the amount of metal particulates or residual carbon entrapped in the oil during its process of use on the basis of the peak value.

Figure 6:
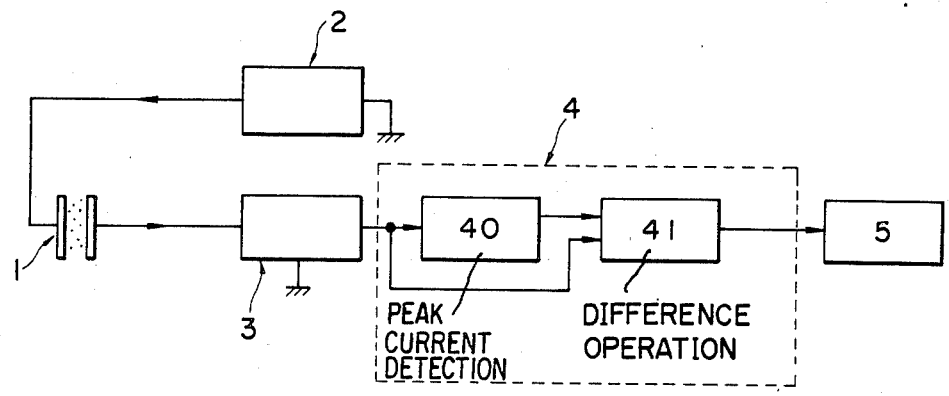

FIG. 6 illustrates a method of and an apparatus for evaluating the performance of a dielectric fluidic substance according to a third embodiment (belonging to the first aspect).

According to the method of the third embodiment, the processing means derives a variation in a fixed period of time at a desired position of a current flowing between the electrodes due to a transient response of the dielectric fluidic substance. The apparatus according to the third embodiment comprises a pair of electordes 1 placed in contacting relation to a dielectric substance to be measured, a voltage source 2 for applying a pulse voltage to the electrodes, a current detecting means 3 for detecting a transient response current flowing through the dielectric substance when the pulse voltage is applied to the electrodes 1, a processing circuit means 4 composed of a peak detecting means 40 for detecting a peak value in a fixed period of time at a desired position of the transient response current detected by the current detecting means 3 and a differential operation means 41, and a display means 5 for displaying an output from the differential operation means 41 as the performance value of the dielectric fluidic substance.

With the method and apparatus thus arranged according to the third embodiment, when a pulse voltage is applied to the dielectric substance contacting the pair of electrodes 1, a variation in a fixed period of time of the current due to a transient response of the dielectric fluidic substance is dependent on a variation of the conductivity of the dielectric fluidic substance. The quantity of water content or large foreign matter such as insolubles in lubricating oil, for example, for automobiles can be determined from the current variation.

Figure 7:
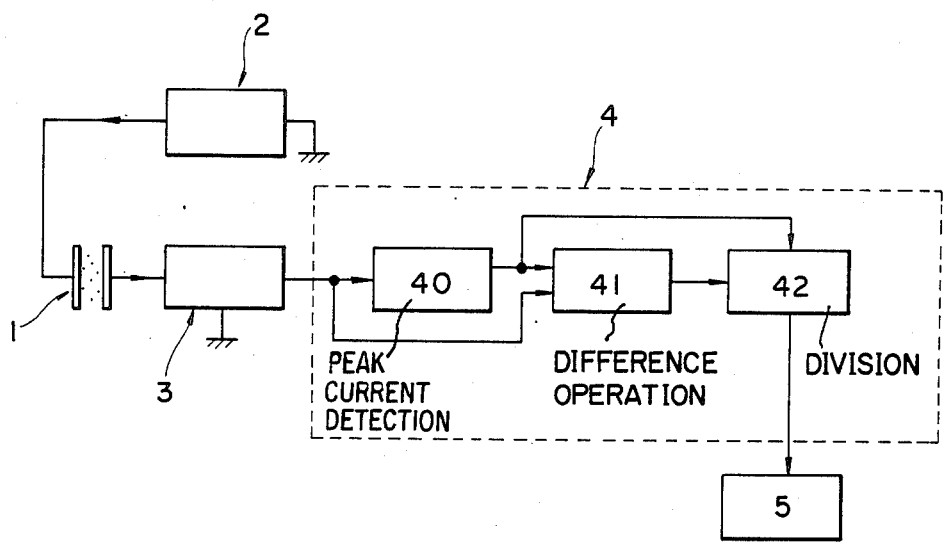
Figure 9A:
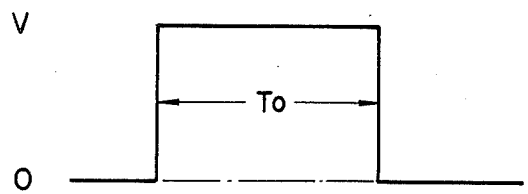
Figure 9B:
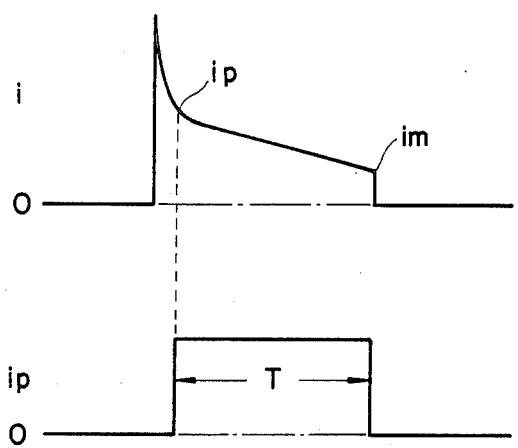
Figure 9C:
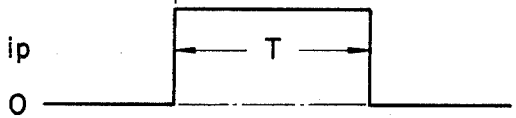
Figure 9D:

FIG. 7 illustrates a method of and an apparatus for evaluating the performance of a dielectric fluidic substance according to a fourth embodiment (belonging to the first aspect).

According to the method of the fourth embodiment, the processing means derives a ratio, through division, of a peak value at a desired position of a current flowing between the electrodes due to a transient response of the dielectric substance to a variation of the current upon elapse of a period of time after the peak value. The apparatus according to the fourth embodiment comprises a pair of electordes 1 placed in contacting relation to a dielectric substance to be measured, a voltage source 2 for applying a pulse voltage to the electrodes, a current detecting means 3 for detecting a transient response current flowing through the dielectric substance when the pulse voltage is applied to the electrodes 1, a processing circuit means 4 composed of a peak detecting means 40 for deriving a ratio of a peak value at a desired position of the transient response current detected by the current detecting means 3 to a current variation in a fixed period of time, a differential operation means 41 and a division means 42, and a display means 5 for displaying an output from the division means 42 as the performance value of the dielectric fluidic substance.

With the method and apparatus thus arranged according to the fourth embodiment, synergic characteristics of a mixture dependent on the conductivity of the dielectric fluidic substance detected by the embodiment of FIG. 5 and a mixture dependent on the variation of the conductivity of dielectric fluidic substance detected by the embodiment of FIG. 6 can be grasped for proper measurement of the performance of the dielectric fluidic substance.

In lubricating oil for automobiles, for example, the amount of an electrically conductive substance such as metal particulates and residual carbon is increased during the process of use, with the result that the peak value of a transient response current flowing when a pulse voltage is applied is increased. As the quantity of water content and dielectric insolubles is increased, the particles of such foreign matter are enlarged to reduce the variation of the transient response current in a fixed period of time. Accordingly, it can be determined that the greater the ratio ip/$\Delta$i computed by the apparatus of the fourth embodiment, the larger the foreign matter particles, so that the performance, contamination, and service life of the lubricating oil can accurately be measured on the basis of the ratio ip/$\Delta$i.

FIG. 8 illustrates a method of and an apparatus for evaluating the performance of a dielectric fluidic substance according to a fifth embodiment (belonging to the second aspect). According to this method, a pulse voltage having a constant amplitude and a constant time duration is applied by the power supply means to the electrodes. According to the apparatus of this embodiment, a voltage source 2 comprises a power supply 20 for generating a desired DC voltage and a switching means 21 for setting a desired time duration. With the method and apparatus thus arranged, a pulse voltage having a desired voltage value and a desired time duration can be applied to a dielectric substance disposed between a pair of electrodes 1. This allows optimum transient response characteristics to be selected for the type of the dielectric substance to be measured for evaluating the performance of the dielectric fluidic substance with maximum sensitivity.

A transient response current flowing through the dielectric fluidic substance between the electrodes 1 when a pulse voltage is applied, is detected by a current detecting means 3 composed of a current-to-voltage converter 30 such as a resistor and a low-pass filter circuit 31 for removing noise included in the transient response current. The current detecting means 3 of such an arrangement can convert the transient response current easily into a voltage signal, and remove noise, with a low-pass filter, mixed into a current signal when the transient response current is measured, especially for a dielectric fluidic substance presenting an extremely high resistance, so that the transient response current can accurately be detected.

A processing circuit means 4 is composed of a gate means 43, a peak detecting means 40, a differential operation means 41, and a division means 42. The gate means 43 is energized by a gate signal supplied from the switching means 21 and delayed a desired period of time with respect to a starting signal for starting the voltage source 2. Accordingly, the transient response current immediately after the pulse voltage has been applied to the electrodes 1 is cut off by the gate means 43 and will not be fed to the peak detecting means 40. Stated otherwise, gate means 43 allows only a current signal to be detected of the transient response current, within a fixed period of time upon elapse of a desired period of time after the pulse voltage has been applied. Thereafter, a peak value upon elapse of the desired period of time selected by the gate means and a variation in the current in a fixed period of time are detected and subjected to a calculation. The processing circuit means 4 produces a signal indiative of the ratio of the peak value to the current variation.

A display means 5 comprises a holding means 50, an analog display or meter 51, a discriminating means 52, and an indicator 53. The ratio of the peak value to the current variation as issued from the processing circuit means 4, at a desired position in a fixed period of time, of the transient response current through the dielectric fluidic substance, is held by the holding means 50 and indicated by the analog meter 51. Thus, the performance of the dielectric fluidic substance can be grasped from an indication on the analog meter 51. The output from the processing means 4 or the output from the holding means 50 is fed to the discriminating means 52, in which it is compared with a desired reference. The result of comparison is then displayed on the indicator 53, which is composed of lamps or the like.

The processing circuit means 4 for detecting a variation or change in a current will be described with reference to signal waveforms shown in FIG. 9.

It is assumed that the pulse voltage generated by the voltage source 1 has a time duration $T_0$ and a voltage value V. When the pulse voltage (FIG. 9 (a)) is impressed on the electrodes 1 between which the dielectric fluidic substance is placed, a transient response current i as illustrated in FIG. 9 (b) flows through the dielectric fluidic substance between the electrodes. An initial value of the current i is expressed by $i = V/r_0$ ($r_0$ is the internal resistance of the circuit), and decreases exponentially. Then, a steady-state current which varies gradually flows for a long period of time. The current variation is caused by the fact that charged particles in the dielectric fluidic substance slowly move toward the electrodes, and serves as the basis for evaluating the performance of the dielectric fluidic substance, as desribed above in the explanation of the principles.

The peak detecting means 40 in the processing circuit means 4 according to the fifth embodiment is capable of detecting a peak value ip of the transient response current flowing a fixed period of time after a pulse voltage of a fixed time duration has been applied (FIG. 9 (c). The transient response current ip detected by the peak detecting means 40 is supplied to one of the input terminals of the differential operation means 41, while the transient response current upon elapse of the fixed period of time is fed to the other input terminal of the differential operation means 41. The differential operation means 41 effects a differential operation on the input signals to detect a variation $\Delta i$ in the transient response current in the fixed period of time (FIG. 9 (d)).

Figure 10:
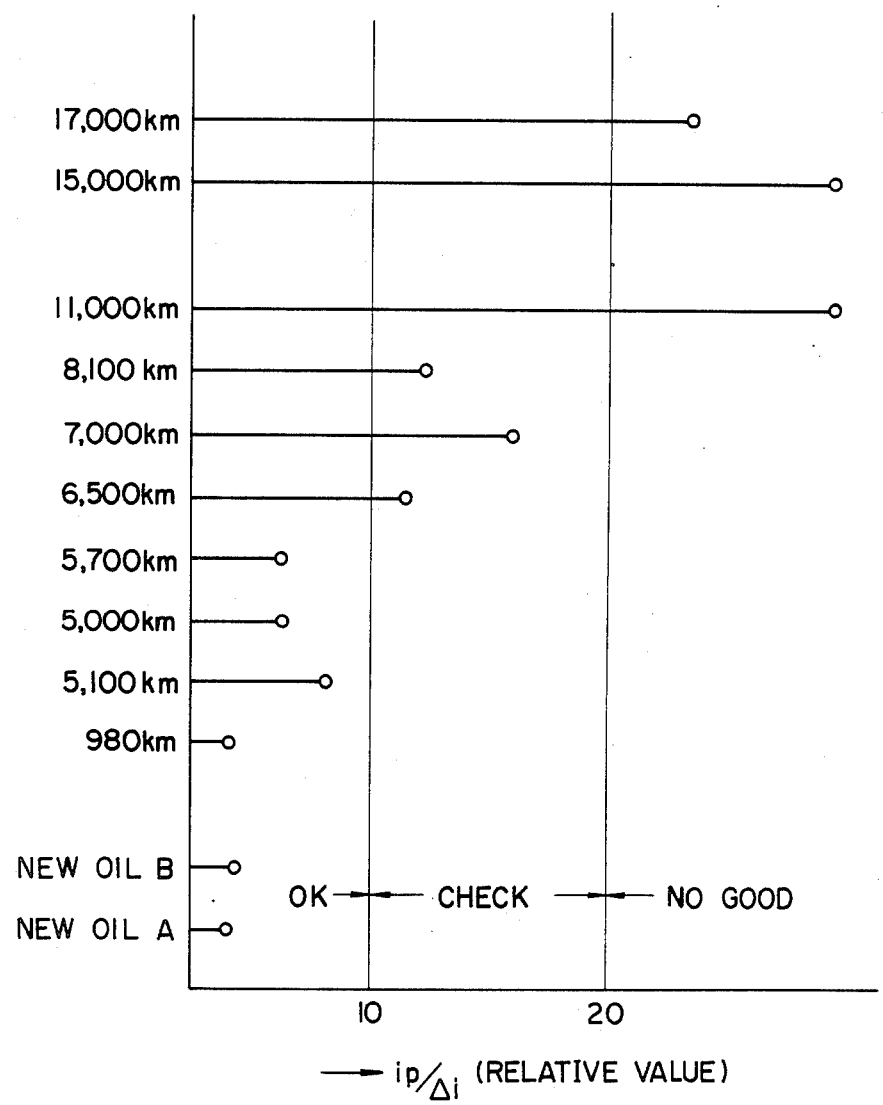

FIG. 10 shows the results of measurement, by the apparatus of FIG. 9, of ratios ip/$\Delta i$ of peak values of the transient response current to variations in a fixed period of time while lubricating oil for automobiles is in use.

FIG. 10 indicates that the ratio ip/$\Delta i$ is 2 or smaller for new oil and oil with the travelled distance of 1,000 km or less, is in the range of from 3 to 5 for oil with the running distance of 5,000 km, and is 16 or higher for oil with the running distance of 10,000 km or more. Accordingly, it is understood that the ratio ip/$\Delta i$ is substantially proportional to the distance that the automobile has travelled. Since the service life of lubricating oil is about 10,000 km in FIG. 10, the reference in the discriminating means 52 in the display means 5 may be selected to indicate "OK" if the ratio ip/i is 6 or less, "CHECK" if the ratio is in the range of from 6 to 12, "NO GOOD" if the ratio is 12 or higher, so that the condition of contamination and service life of the lubricating oil can accurately be determined.

Although the voltage output from the DC voltage source 20 is shown in FIG. 8 as being converted into a pulse voltage by the switching means 21, the voltage source 2 may be arranged to produce a pulse voltage directly without such conversion. While the division means 42 in the processing circuit means 4 has been described as effecting a dividing operation with the peak value ip of the transient response current serving as the numerator and the variation $\Delta i$ as the denominator, the division means 42 may effect an inverted dividing operation.

Figure 11:
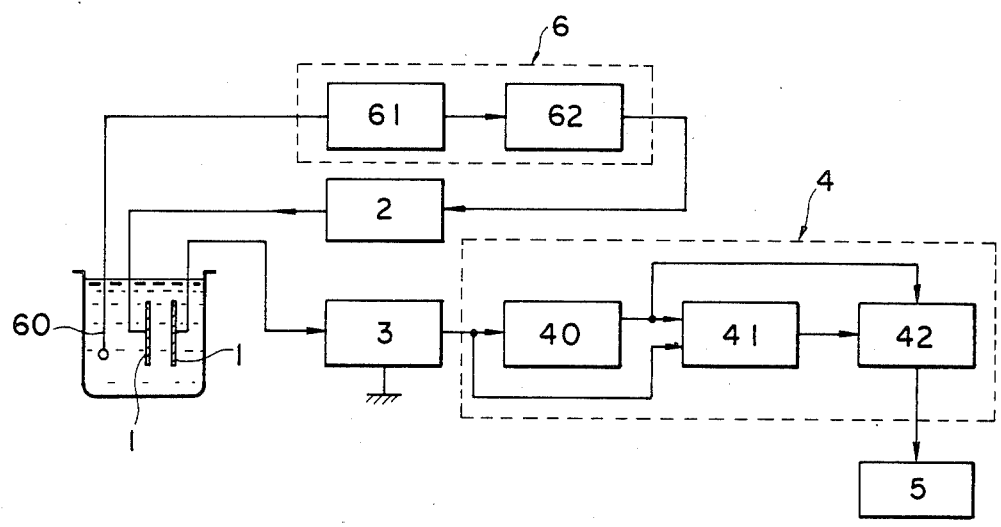
FIG. 11 is a block diagram showing a sixth embodiment of the invention.

FIG. 11 illustrates a method of and an apparatus for evaluating the performance of a dielectric fluidic substance according to a sixth embodiment (belonging to the third aspect) of the present invention.

According to this method, a pulse voltage is applied by a power supply means 2 to at least a pair of electrodes 1 contacting a dielectric fluidic substance to be measured when the dielectric fluidic substance is at a prescribed temperature as detected by a temperature detecting means, and a transient response current flowing between the electrodes dependent on the property of the dielectric fluidic substance disposed between the electrodes 1 is measured to evaluate the performance of the dielectric fluidic substance based on the measured current.

The apparatus according to the sixth embodiment comprises, as shown in FIG. 11, a pair of electrodes 1 disposed in an oil pan or transmission of an automobile, for example, in contacting relation to lubricating oil, a temperature detecting means 6 composed of a temperature sensor 60, a temperature detecting circuit 61, and a command signal generating circuit 62 for measuring the temperature of the lubricating oil and issuing a command signal to measure the performance of the lubricating oil when the lubricating oil temperature is in a prescribed range, a voltage source 2 for applying a pulse voltage to the electrodes when the lubricating oil temperature is in the prescribed range, a current detecting means 3 for detecting a transient response current flowing through the lubricating oil between the electrodes 1, a processing circuit means 4 composed of a peak detecting circuit 40 for detecting a peak value at a desired position of the transient response current, a differential operation circuit 41 for detecting a variation in the transient response current in a fixed period of time after the peak value, and a computing circuit 42 for determining a ratio of the peak current value to the current variation, and a display means 5 responsive to an output from the processing circuit means 4 for displaying the performance, the condition of contamination, and the service life of the lubricating oil.

More specifically, according to the method of the sixth embodiment, when the dielectric fluidic substance to be measured is at a prescribed temperature, the temperature is detected by the temperature detecting means 6 and a pulse voltage is applied by the voltage source 2 to the electrodes 1 contacting the dielectric fluidic substance, a current flowing between the electrodes 1 dependent on the property of the dielectric fluidic substance disposed between the electrodes 1 is detected by the current detecting means 3, a variation in the current is measured by a processing means 4, and the measured value and the performance of the dielectric fluidic substance are diplayed by a display means 5, so that the performance of the dielectric fluidic substance can be measured from transient response characteristics of the dielectric fluidic substance at the time the pulse voltage is applied.

In the method and apparatus thus arranged according to the sixth embodiment, a current variation in a fixed period of time in the transient response characteristics of the lubricating oil manifests itself in a certain temperature of engine oil. As a consequence, the temperature detecting means 6 is effective in determining the performance of lubricating oil with high sensitivity and reliability.

A seventh embodiment based on the sixth embodiment of FIG. 11 will be described with reference to FIG. 12. Identical parts in FIG. 12 are denoted by identical reference characters in FIG. 11, and will not be described in detail.

An apparatus according to the seventh embodiment comprises a pair of electrodes 1 disposed in contacting relation to lubricating oil such as engine oil, and a temperature measuring means 6 composed of a temperature sensor 60 for detecting the temperature of the lubricating oil, a temperature detecting circuit 61 for detecting a temperature signal based on an output from the temperature sensor 60, and a command signal generating circuit 62 responsive to an output from the temperature detecting circuit 61 for determining whether the temperature of the lubricating oil is in a measurement temperature range and generating a command signal having a constant time duration. The apparatus also includes a pulse power supply means 2 composed of a starting circuit 22 for starting a measuring operation in response to an output from the temperature measuring means 6 and a starting signal supplied from an external source, a power supply 20 for generating a DC voltage, and a switching circuit 21 responsive to a signal a of a constant time duration from the starting circuit 22 for effecting switching operation on an output from the power supply 20 to apply a pulse voltage of a fixed amplitude and a fixed time duration to the electrodes 1. A current detecting means 3 comprises a current detecting element 30 for measuring a transient response current flowing between the electrodes 1 due to a transient response of the dielectric fluidic substance disposed between the electrodes 1 and a low-pass filter 31 for removing noise contained in the transient response current signal. The apparatus of FIG. 12 also has a processing circuit means 4 composed of a gate circuit 43 energizable by a gate signal b of a fixed time duration which is produced by the starting circuit 22 and delayed a fixed period of time with respect to the starting signal a applied to energize the switching circuit 21, a peak detecting circuit 40 for holding a peak value, at a desired position in a fixed period of time, of an output from the gate circuit 43, that is, the transient response current signal for the lubricating oil, a differential operation circuit 41 supplied with an output from the peak detecting circuit 40 and the transient response current in the fixed period of time from the gate circuit 43 for measuring a variation of the transient response current in the fixed period of time, and a division circuit 42 supplied with the output from the peak detecting circuit 40 and an output from the differential operation circuit 41 for measuring a ratio of the peak value at the desired position of the transient response current to the current variation in the fixed period of time. The apparatus further comprises a display circuit means 5 composed of a holding circuit 50 responsive to an output signal from the processing circuit means 4 for temporarily holding the result of division, an indication meter 51 such as an analog meter for indicating an output from the holding circuit 50, a discriminating circuit 52 for comparing an output from the processing circuit means 4 or an output from the holding circuit 50 with an output from a dicrimination reference memory 53 which can establish a desired dicrimination reference, and an indicator 54 responsive to an output from the discriminating circuit 52 for indicating whether the performance of the lubricating oil is acceptable or not with lamps or the like.

With the method and apparatus according to the seventh embodiment, when the temperature of the lubricating oil falls within the measurement temperature range, the starting circuit 22 is actuated by a starting signal applied from an external source to cause the pulse power supply means 2 to apply a pulse voltage of a fixed amplitude and a fixed time duration to the electrodes 1 held in contact with the lubricating oil. A current now flows between the electrodes 1 due to a transient response of the lubricating oil.

The transient response current is detected by the current detecting means 3 and then is subjected to computing operation in the processing circuit means 4 for determining a ratio of a peak value, at a desired position in a fixed period of time, of the transient response current to a variation in the current. Based on the determined ratio, the performance, condition of contamination, and service life of the lubricating oil are displayed by the display means 5.

The apparatus thus constructed and operated allows an automobile driver, for example, to grasp the performance of lubricating oil in a simple process, and also to know a proper time when the lubricating oil should be replaced with new lubricating oil based on the results of measurement.

According to the embodiment of FIG. 12, that the dielectric fluidic substance to be measured falls within the measurement temperature range means that the dielectric fluidic substance is in a temperature condition effective to grasp the performance thereof. Such a temperature condition is called a maximum sensitivity range, which is about 5° C. to 70° C. for various engine oils, typically lubricating oil used in automobiles and ships. In the maximum sensitivity range, the temperature detecting means 6 is operated to apply a pulse voltage to the electrodes.

An optimum measurement temperature in the above temperature range means a temperature range including a normal temperature and temperatures slightly higher and lower than the normal temperature. The temperature range for coolant oil and lubricating oil such as cutting oil is substantially the same as described above.

In the method and apparatus for measuring the performance of lubricating oil according to the seventh embodiment, the power supply means for generating a pulse voltage may have an inverter for converting a voltage from a battery on an automobile or a primary voltage signal generated by an igniter on a gasoline engine into a DC voltage.

Where the apparatus is incoporated in an automobile, a maximum sensitivity is obtained when the amplitude of the pulse voltage ranges from 100 to 300 V with the electrodes 1 spaced 1 mm from each other. Since the property (varied by additives) of lubricating oil differs from type to type and dependent on the site of application, the power supply means should be arranged more advantageously to vary the amplitude of a pulse voltage generated thereby for a wider range of aplications.

The electrodes held in contact with the dielectric fluidic substance may comprise parallel plate electrodes, cylindrical electrodes, multilayer electrodes, or mesh electrodes provided they can cause a transient response of lubricating oil. Where the electrodes comprise parallel plates or cylindrical members, they should preferably be placed in an area in which the lubricating oil runs at all times, for example, at an outlet of an oil cleaner for engine oil, or be arranged normally to the surface of the lubricating oil in an oil pan, so that no foreign matter will be deposited between electrodes.

The temperature sensor 60 for detecting the temperature of the lubricating oil may be of a unitized construction integral with the electrodes, or may be arranged separately from the electrodes. Instead of the temperature sensor 60, an output from a water temperature sensor generally used in automobiles may be utilized for the same operation and advantages as described above.

It is preferable that the pulse voltage produced by the power supply means should have a single pulse. More specifically, the lubricating oil is tentatively charged by a transient response of the lubricating oil between the electrodes when the pulse voltage is applied to the electodes. By effecting a next measurement after the charge has completely been eliminated, the influence of the charge in the previous measurement can be removed for accurate measurement.

An eighth embodiment showing a preferred example of the electrodes will be described.

FIG. 13 illustrates a construction of parallel plate electrodes. Electrodes 1 are mounted on an insulating member 1A disposed in a support 1B and are connected by a lead wire 1C to the pulse voltage source and the current detecting means. Where the electrodes are to be installed in an engine oil pan, they should be arranged normally to the surface of oil so that the oil will flow in the direction of the arrows. The electrodes thus constructed can effectively be used as electrodes in the previous embodiment and all other embodiments of the present invention to the same advantages.

FIG. 14 shows a method of and an apparatus for evaluating the performance of a dielectric fluidic substance according to a ninth embodiment (belonging to the fourth aspect) of the present invention.

The apparatus illustrated in FIG. 14 comprises a measuring container 7 having at least a pair of electrodes 1 for containing a dielectric fluidic substance therein between the electrodes 1, a temperature controlling means 6 for controlling the temperature of the dielectric fluidic substance in the measuring container to be a prescribed temperature, a power supply means 2 energizable by an output from the temperature controlling means 6 for applying a pulse voltage to the electrodes 1 in the measuring container 7, a current detecting means 3 for detecting a transient response current flowing through the dielectric fluidic substance due to a transient response thereof when a pulse voltage is applied between the electrodes, a processing circuit means 4 for measuring a peak value at a desired position of the transient response current, a variation of the current in a fixed period of time, and a ratio of the peak value to the current variation, and a display means 5 for displaying an output signal from the processing circuit means 4 as the performance value of the dielectric fluidic substance.

More specifically, the measuring container 7 is composed of a receptacle 70 made of an insulating material, the pair of electrodes 1 mounted on inner walls of the receptacle 70, a temperature sensor 60 for detecting the temperature of lubricating oil in the receptacle 70, and a temperature controlling element 71 for heating or cooling the temperature of the oil in the receptacle 70. The electrodes 1 disposed in the receptacle 70 may comprise parallel plates, cylindrical members, or multilayer electrodes. The temperature controlling element 71 may be composed of a semiconductor device having a Peltier effect, so that by controlling the direction of flow of the current through the semiconductor device, the receptacle 70 may be heated or cooled as desired for controlling the temperature of the dielectric fluidic substance to be a prescribed temperature.

The temperature controlling means 6 is composed of a temperature detecting circuit 61 for converting an output from the temperature sensor 60 into a temperature signal, a temperature controlling circuit 63 responsive to an output from the temperature detecting circuit 61 for heating or cooling the dielectric fluidic substance in the measuring container 1 to a prescribed temperature, and a signal generating circuit 62 for generating a command signal to start a measuring operation when the output from the temperature detecting circuit 61 becomes a predetermined value. With this construction, the temperature controlling means 6 is operated dependent on the temperature of the dielectric fluidic substance in the measuring container 7 to control the temperature of the dielectric fluidic substance in the measuring container 7 to be a prescribed temperature.

The power supply means 2 comprises a starting circuit 22 for starting a measuring operation in response to the output from the temperature controlling means 6 and a starting signal fed from an external source, a power supply 20 for generating a DC voltage, and a switching circuit 21 for effecting switching on the output from the power supply 20 with a signal of a fixed time duration supplied from the starting circuit 22 to apply a pulse voltage of a fixed amplitude and a fixed time duration to the electrodes 1.

The current detecting means 3 is composed of a current detecting element 30 for measuring a transient response current flowing between the electrodes 1 due to a transient response of the dielectric fluidic substance between the electrodes 1 when the pulse voltage is applied to the electrodes 1 by the power supply means 2, and a low-pass filter 31 for removing noise from the transient response current. When measuring a transient response current through a dielectric fluidic substance having an extremely high resistance, the low-pass filter 31 can remove noise picked up by the electrodes 1 in the measuring container 7 and signal lines connecting the electrodes 1 to the current detecting means 3, for permitting only the transient response current to be measured to a nicety.

The processing circuit means 4 comprises a gate circuit 43 energizable by a gate signal of a fixed time duration which is produced by the starting circuit 22 and delayed a fixed period of time with respect to the starting signal applied to energize the switching circuit 21, a peak detecting circuit 40 for holding a peak value, at a desired position in a fixed period of time, of an output from the gate circuit 43, that is, the transient response current signal for the dielectric substance, a differential operation circuit 41 supplied with an output from the peak detecting circuit 40 and the transient response current in the fixed period of time from the gate circuit 43 for measuring a variation of the transient response current in the fixed period of time, and a division circuit 42 supplied with the output from the peak detecting circuit 40 and an output from the differential operation circuit 41 for measuring a ratio of the peak value at the desired position of the transient response current to the current variation in the fixed period of time.

The display means 5 comprises a holding circuit 50 for temporarily holding an output signal from the processing circuit means 4, a reference circuit 53 for holding a discrimination reference value dependent on the property and type of the dielectric fluidic substance, a discriminating circuit 52 supplied with outputs from the holding circuit 50 and the reference circuit 53 for determining the performance of the dielectric fluidic substance or correcting the output from the holding circuit 50 with the reference value, and an indicator 54 composed of an analog meter or lamps for indicating an output from the discriminating circuit 52 as the performance value, remaining life, or service life of the dielectric fluidic substance dependent on the result of measurement of the performance of the dielectric fluidic substance. The reference circuit 53 can vary its performance discrimination value dependent on the property and type of the dielectric fluidic substance to be measured for proper performance determination.

More specifically, where the performance of lubricating oil for automobiles is to be evaluated, the peak value and variation of the transient response current flowing through the dielectric fluidic substance vary dependent on the kind of an additive in the lubricating oil. Thus, the ratio of the peak value and variation of the current is varied dependent on the property and type of the lubricating oil to be measured, so that oil performance can accurately be determined.

The indicator 54 may be arranged to display not only the performance value or service life of the lubricating oil at the time it is measured, but also a remaining life of the lubricating oil by holding an initial performance value of the lubricating oil at the time it is not used in the reference circuit 61 and comparing the determined performance value with the initial performance value, if the property and type of the lubricating oil to be measured is known.

In the apparatus thus constructed according to the ninth embodiment, when the temperature of a dielectric fluidic substance to be measured in the measuring container 7 reaches a prescribed temperature, the starting circuit 22 is actuated by a starting signal from an external source to cause the power supply means 2 to apply a pulse voltage of a fixed amplitude and a fixed time duration to the electrodes 1 in the measuring container 7 which are in contact with the dielectric fluidic substance, whereupon a current due to a transient response of the dielectric fluidic substance flows between the electrodes 1. The transient response current is detected by the current detecting means 3 and then is subjected to computing operation in the processing circuit means 4 for determining a ratio of a peak value, at a desired position in a fixed period of time, of the transient response current to a variation in the current. Based on the determined ratio, the performance, condition of contamination, and service life of the lubricating oil are displayed by the display means 5.

The apparatus thus constructed and operated allows an automobile driver, for example, to grasp the performance of lubricating oil in a simple process, and also to know a proper time when the lubricating oil should be replaced with new lubricating oil based on the results of measurement.

A tenth embodiment of the present invention which is directed to a preferred example of a measuring container will be described with reference to FIGS. 15(a) through 15(c).

Figure 15A:
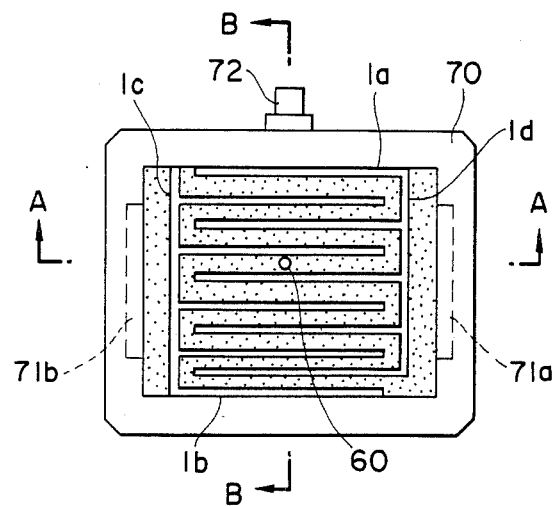
FIGS. 15(a) through 15(c) are cross sectional views of a measuring container according to a tenth embodiment of the present invention, FIG. 15(a) being a plan view of the measuring container, FIG. 15(b) a cross-sectional view taken along line A—A of FIG. 15(a), and FIG. 15(c) a cross-sectional view taken along line B—B of FIG. 15(a)
Figure 15B:
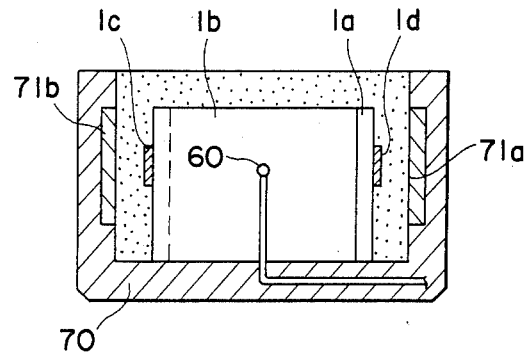
Figure 15C:
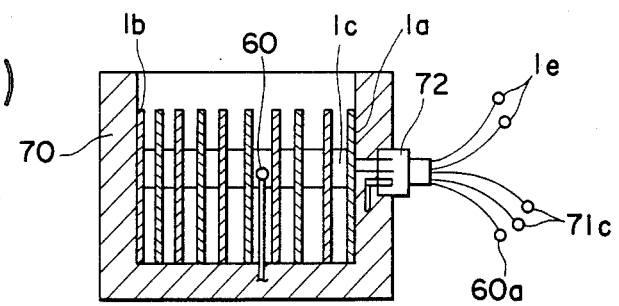

FIG. 15(a) is a plan view of a measuring container 7, FIG. 15(b) is a cross-sectional view taken along line A—A of FIG. 15(a), and FIG. 15(c) is a cross-sectional view taken along line B—B of FIG. 15(a). The measuring container 7 comprises a receptacle 70 made of an insulating material such as a resin material, electronic cooling elements 71a, 71b having a Peltier effect and mounted on opposite inner sides of the receptacle 70, electrode plates 1a, 1b arranged as multiple layers from other inner sides of the receptacle 70, connector plates 1d, 1c electrically connecting the electrodes 1a, 1b, respectively, a temperature sensor 60 disposed substantially centrally in the receptacle 70 out of contact with the electrode plates 1a, 1b, and a connector 72 through which lead wires 1e extending from the electrode plates 1a, 1b, lead wires 71c extending from the electronic cooling elements 71a, 71b, and a lead wire 60a extending from the temperature sensor 60 are led out for connection to an evaluating apparatus according to the present invention.

For evaluating the performance of lubricating oil for automobiles, for example, the electrodes arranged as multiple layers in the receptacle 70 can measure, with a high sensitivity, transient response characteristics of the lubricating oil placed in the receptacle 70 at the time a pulse voltage is applied to the electrodes. More specifically, the electrodes have an increased area of contact with the lubricating oil so that the quantity of charged particles produced by electrolytic dissociation of the lubricating oil disposed between the electrodes can be increased. This increases signals indicating a peak value and a variation of the transient response current, and hence an arithmetic operation to determine a ratio of the peak value to variation of the current can be effected with a high degree of accuracy. As a consequence, the performance of lubricating oil can be measured with higher accuracy.

The temperature controlling elements 71 are disposed on the opposite inner sides of the receptacle 70 and the temperature sensor 60 is placed centrally in the receptacle 70 for controlling the temperature of the lubricating oil in the receptacle 70 substantially uniformly throughout its entire quantity to a prescribed temperature.

The electrode plates 1a, 1b may be detachably mounted in the receptacle 70 for the purpose of cleaning the receptacle 70 and the electrode plates 1a, 1b.

A method of and an apparatus for evaluating the performance of a dielectric fluidic substance according to an eleventh embodiment (belonging to the fifth aspect) of the present invention will be described.

According to the eleventh embodiment, when a dielectric fluidic substance to be measured is at a prescribed temperature, the temperature is detected by a temperature detecting means, and a pulse voltage is applied by a power supply means to at least a pair of electrodes contacting the dielectric fluidic substance. A transient response current flowing at this time through the dielectric fluidic substance between the electrodes dependent on the property of the dielectric fluidic substance between the electrodes is detected by a current detecting means, and at least one of a peak value at a desired position of the transient response current, a variation of the current at the desired position in a fixed period of time, and a ratio of the peak value to the variation of the current is computed by a processing circuit means. The peak value of the current is regarded as a liquid level of the dielectric fluidic substance, and the ratio is displayed as the performance of the dielectric fluidic substance by a display means. Thus, the liquid level and performance of the dielectric substance are measured from the transient response current.

The method of evaluating a dielectric fluidic substance according to this embodiment is as described in the above description of the principles. The princples of measuring a liquid level of a dielectric fluidic substance according to the eleventh embodiment will now be described with reference to FIGS. 16 and 17. The principles and the embodiment of the apparatus will be described in which lubricating oil for automobiles is employed as a typical example of a dielectric fluidic substance.

Figures 16A, 16B:
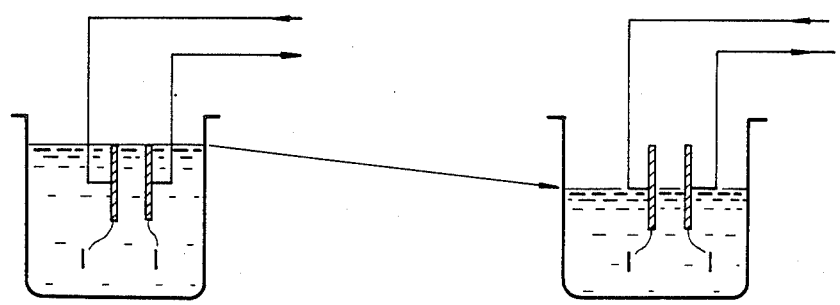
FIGS. 16 and 17 are views of an eleventh embodiment, FIGS. 16(a) and 16(b) being diagrams showing the principles of measuring a liquid level of the dielectric fluidic substance, and FIGS. 17(a) through 17(d) representations of the results of measurement.
Figure 17A:
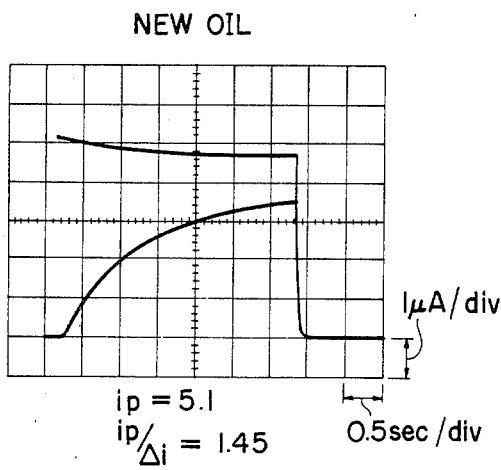
Figure 17B:
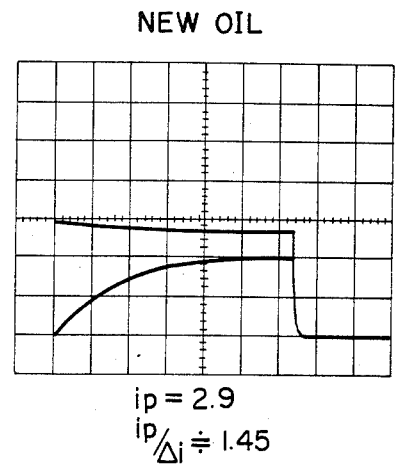
Figure 17C:
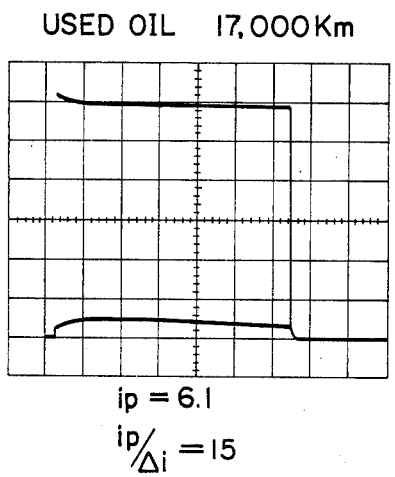
Figure 17D:
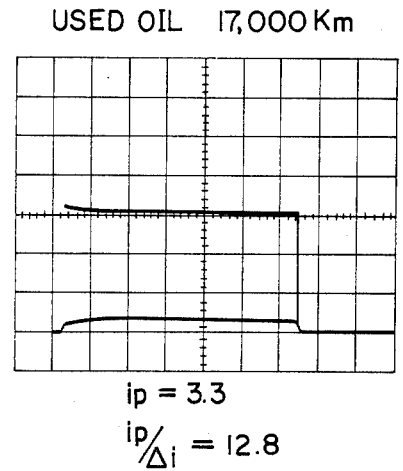

FIG. 16(a) shows a pair of electrodes 1 positioned bodily in lubricating oil. When a pulse voltage is applied to the electrodes 1, a transient response current flows through the lubricating oil between the electrodes as shown in FIG. 17(a) for new oil and as shown in FIG. 17(c) for oil with a running distance of 17,000 km. FIG. 16(b) shows a pair of electrodes 1 with their halves positioned in lubricating oil. A transient response current flows through the lubricating oil between the electrodes of FIG. 16(b) as shown in FIG. 17(b) for new oil and as shown in FIG. 17(d) for oil with a running distance of 17,000 km. The currents shown in FIGS. 17(a) through 17(d) can be derived from the output from the gate means 43 in the processing circuit means 4 and the output from the differential operation means 41 in the embodiment shown in FIG. 8.

It will be understood from these experimental facts that the peak value at any desired position of the transient response current varies in proportion to the oil level. This is because the total electric resistance of the lubricating oil in the area of contact between the electrodes 1 and the lubricating oil varies since the area of contact is changed.

The level of the lubricating oil held in contact with the electrodes can be detected on the basis of a peak value at any desired position of a transient response current flowing through the lubricating oil between the electrodes by applying a pulse voltage to the pair of electrodes.

However, since the peak current value differs dependent on the property (dependent on an additive) of the lubricating oil and the manner in which the performance of the lubricating oil varies, no correct oil level can be measured merely by measuring the peak current value. For measuring an oil level based on the peak current value, an initial value (a peak current value before oil is used) $ip_0$ is stored at the time of oil replacement, and a peak value $ip_1$ of the current in its process of use is subtracted from the initial value $ip_0$. The oil level can now be measured from the value $ip_0 - ip_1$ irrespective of the type of lubricating oil.

Even as far as the same type of lubricating oil is concerned, the conductivity thereof becomes increased under the influence of metal particulates and residual carbon as the oil performance is lowered in its process of use as shown in FIGS. 17(c) and 17(d). The peak current value is increased as compared with new oil.

In view of the foregoing facts, it is possible in reducing the present invention to practice to measure a liquid level of lubricating oil accurately in its use by effecting the following calculation:

$$ip_0 - \frac{1}{K} ip_1 \ldots (K \propto ip/\Delta i)$$

where K is a coefficient varying with the ratio ($ip/\Delta i$) of the peak current value and the current variation that are measured as values indicative of the performance of the lubricating oil.

Figure 18:
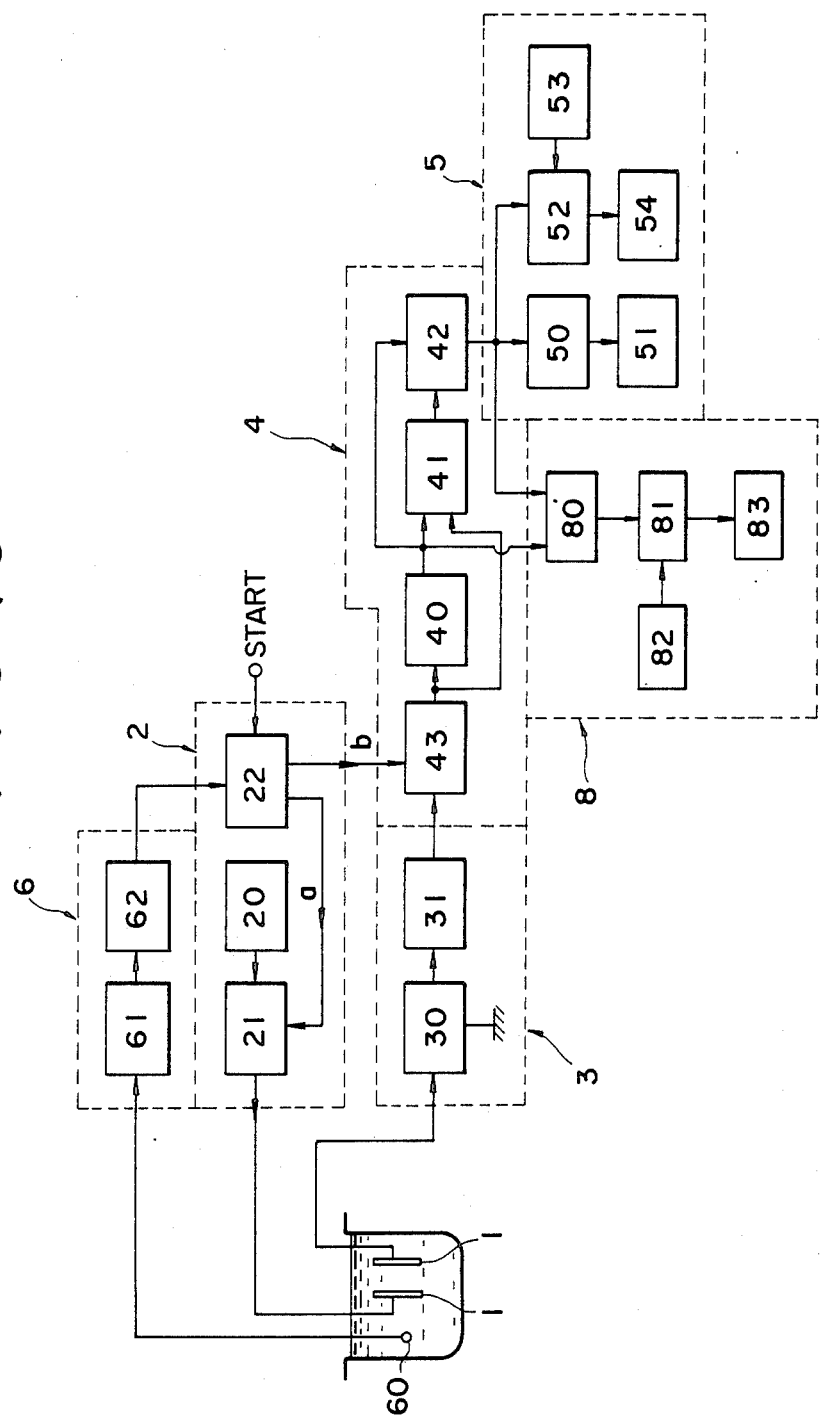
FIGS. 18 through 20 are block diagrams of twelfth to fourteenth embodiments.

FIG. 18 shows a twelfth embodiment (belonging to the fifth aspect) of the present invention.

The apparatus according to the twelfth embodiment comprises a pair of electrodes 1 disposed in contacting relation to lubricating oil such as engine oil, and a temperature measuring means 6 composed of a temperature sensor 60 for detecting the temperature of the lubricating oil, a temperature detecting circuit 61 for detecting a temperature signal bsed on an output from the temperature sensor 60, and a command signal generating circuit 62 responsive to an output from the temperature detecting circuit 61 for determining whether the temperature of the lubricating oil is in a measurement temperature range and generating a command signal having a constant time duration. The apparatus also includes a pulse power supply means 2 composed of a starting circuit 22 for starting a measuring operation in response to an output from the temperature measuring means 6 and a starting signal supplied from an external source, a power supply 20 for generating a DC voltage, and a switching circuit 21 responsive to a signal a of a constant time duration from the starting circuit 22 for effecting switching operation on an output from the power supply 20 to apply a pulse voltage of a fixed amplitude and a fixed time duration to the electrodes 1. A current detecting means 3 comprises a current detecting element 30 for measuring a transient response current flowing between the electrodes 1 due to a transient response of the dieletric fluidic substance disposed between the electrodes 1 and a low-pass filter 31 for removing noise contained in the transient response current signal.

The apparatus of FIG. 18 also has a processing circuit means 4 composed of a gate circuit 43 energizable by a gate signal b of a fixed time duration which is produced by the starting circuit 22 and delayed a fixed period of time with respect to the starting signal a applied to energize the switching circuit 21, a peak detecting circuit 40 for holding a peak value, at a desired position in a fixed period of time, of an output from the gate circuit 43, that is, the transient response current signal for the lubricating oil, a differential operation circuit 41 supplied with an output from the peak detecting circuit 40 and the transient response current in the fixed period of time from the gate circuit 43 for measuring a variation of the transient response current in the fixed period of time, and a division circuit 42 supplied with the output from the peak detecting circuit 40 and an output from the differential operation circuit 41 for measuring a ratio of the peak value at the desired position of the transient response current to the current variation in the fixed period of time.

The apparatus further comprises a display circuit means 5 composed of a holding circuit 50 responsive to an output signal from the processing circuit means 4 for temporarily holding the result of division, an indication meter 51 such as an analog meter for indicating an output from the holding circuit 50, a discriminating circuit 52 for comparing an output from the processing circuit 52 or an output from the holding circuit 50 with an output from a discrimination reference memory 53 which can establish a desired discrimination reference, and an indicator 54 responsive to an output from the discriminating circuit 52 for indicating whether the performance of the lubricating oil is acceptable or not with lamps or the like.

In addition, the apparatus has an oil level display means 8 comprising a scale-factor circuit 80 for correcting the peak value ip at the desired position of the transient response current from the peak detecting circuit 40 with a coefficient K indicative of a ratio $ip/\Delta i$ of the peak value ip at the desired position of the transient response current to the current variation $\Delta i$ in a fixed period of time after the desired postion, which are issued from the division circuit 42 and repsentative of the performance of the lubricating oil, a memory 82 for storing an initial performance value of the lubricating oil, that is, the peak current value $ip_0$ for the lubricating oil prior to its use, a differential operation circuit 81 for computing the difference between a peak current value $ip \cdot 1/k$ corrected dependent on the condition of performance of the lubricating oil at the time of measurement and a reference value $ip_0$ stored in the memory 82, and an oil level meter 83 for displaying an output from the differential operation circuit 81 as the oil level of the lubricating oil.

With the method and apparatus thus arranged according to the twelfth embodiment, when the temperature of the lubricating oil falls within the measurement temperature range, the starting circuit 22 is actuated by a starting signal applied from an external source to cause the pulse power supply means 2 to apply a pulse voltage of a fixed amplitude and a fixed time duration to the electrodes 1 held in contact with the lubricating oil. A current now flows between the electrodes 1 due to a transient response of the lubricating oil.

The transient response current is detected by the current detecting means 3 and then is subjected to computing operation in the processing circuit means 4 for determining a ratio of a peak value, at a desired position in a fixed period of time, of the transient response current to a variation in the current. Based on the determined ratio, the performance, condition of contamination, and service life of the lubricating oil are displayed by the display means 5.

The above apparatus for measuring the performance and liquid level of the lubricating oil allows an automobile driver, for example, to grasp the performance of lubricating oil in a simple process, and also to know a proper time when the lubricating oil should be replaced with new lubricating oil based on the results of measurement.

While the lubricating oil is at rest, or while the engine of an automobile, for example, is stopped, a peak value at a desired position of the transient response current for lubricating oil before it is used is compared with a peak value of the transient response current at the present time to make it possible for the lubricating oil level to be easily measured. Where the measuring apparatus of the above embodiment is installed on an automobile, it is rendered possible to let the driver know the exact amount of remaining lubricating oil, so that an engine trouble due to the shortage of lubricating oil can be prevented.

The apparatus according to the twelfth embodiment may have only one of the capabilities of measuring the performance and oil level of the lubricating oil, or a combination of both capabilities.

A preferred example of an electrode assembly according to the twelfth embodiment will be described according to a thirteenth embodiment.

Figure 19:
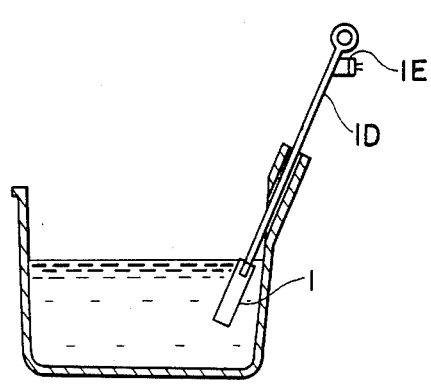

FIG. 19 shows an electrode assembly designed for use in an automobile, the electrode assembly being illustrated as being mounted on an oil level gauge of a conventional construction.

An electrode assembly is disposed on a distal end of a gauge support 1D with signal wires from the electrode assembly extending through the gauge support 1D out to an upper end of the gauge support 1D for connection to a connector 1E. This arrangement allows the electrode assembly to be detachably coupled to the power supply means 2, the temperature detecting means 6, and the current detecting means 3 as shown in FIG. 18.

Accordingly, where the electrode assembly is used on an automobile, for example, at all times, the measuring apparatus may be positioned on the instrument panel and may be connected to the electrode assembly through the connector. Where the measuring apparatus is not installed on an automobile, the connector 1E of the electrode assembly may be used only when measuring the performance and level of the lubricating oil. Where both the electrode assembly and the measuring apparatus are not installed on an automobile, for example, the conventional oil level gauge should be removed and the oil level gauge with the electrode assembly of the illustrated embodiment attached should instead be inserted for measuring the performance and level of the lubricating oil. Since the electrode assembly is used for measuring the performance and level of the lubricating oil, it is not necessary to form the electrode assembly as a unitary construction integral with the oil level gauge, but the electrode assembly may be located anywhere provided it can be brought into contact with the lubricating oil.

Figure 20:
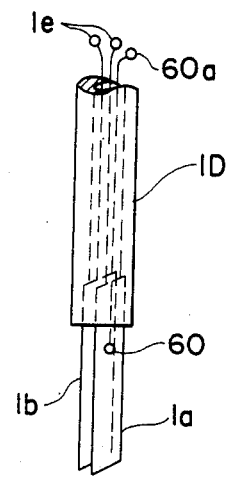

FIG. 20 is illustrative of a preferred example of an electrode assembly according to a fourteenth embodiment of the present invention. The electrode assembly is composed of electrodes 1a, 1b metal fixedly mounted in a hollow gauge support 1D of an insulating material and spaced a suitable distance from each other. Signals wires 1c extend respectively from the electrodes 1a, 1b through the bore in the gauge support 1D out of the latter. A temperature sensor 60 such as a thermistor for detecting the temperature of the lubricating oil is fixed to the gauge support 1D. A singal wire 60a extends from the temperature sensor 60 through the bore in the gauge support 1D out of the latter. With this construction, the performance and level of engine oil contained in an oil container of the engine of an automobile can simultaneously be measured simply by inserting the electrode assembly into the oil container, according to the measuring principles of the present invention.

Figure 21A:
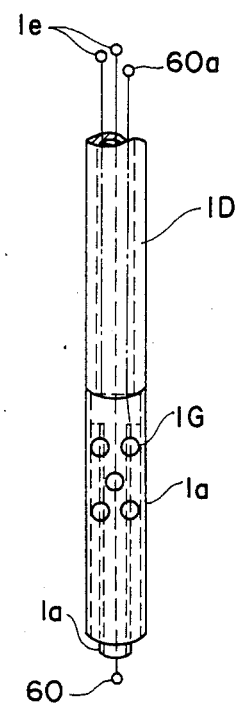
FIGS. 21(a) and 21(b) are illustrative of an electrode assembly according to a fifteenth embodiment of the present invention, FIG. 21(a) being a side elevational view of the electrode assembly and FIG. 21(b) a cross-sectional view.
Figure 21B:
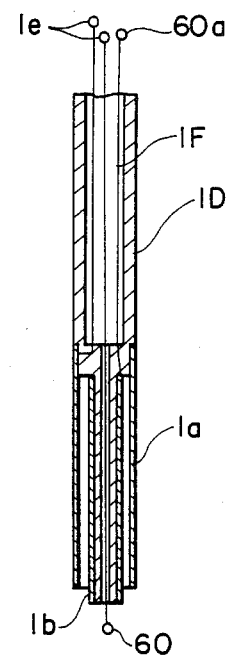
Figure 22:
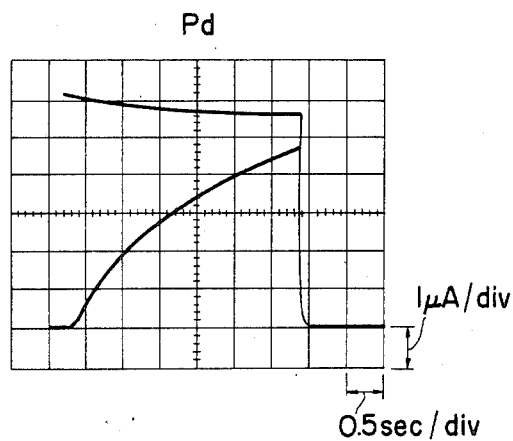
FIGS. 22 through 25 are representations of measured transient response currents flowing when the electrode assembly of a sixteenth embodiment is employed, FIG. 22 being illustrative of the current when the electrodes are of palladium, FIG. 23 the current when the electrodes are of copper, FIG. 24 the current in the case of brass, and FIG. 25 the current in the case of stainless steel.
Figure 23:
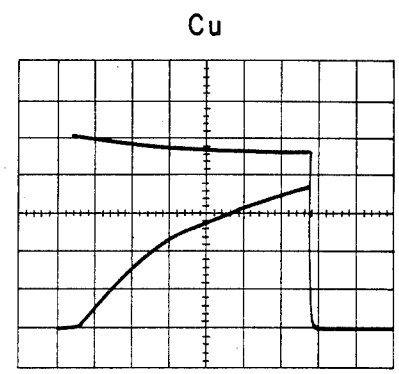
Figure 24:
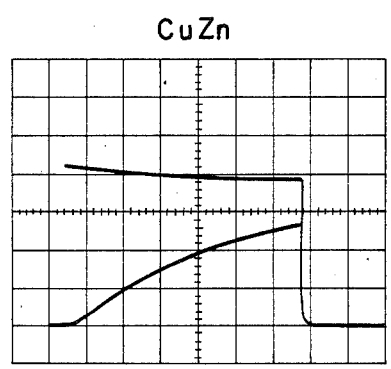
Figure 25:
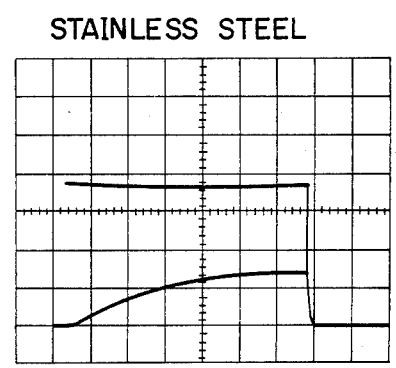

FIG. 21(a) is an elevational view of an electrode assembly according to a fifteenth embodiment of the present invention, and FIG. 21(b) is a cross-sectional view of the electrode assembly. The electrode assembly is of a cylindrical shape composed of an inner electrode 1b of metal and an outer electrode 1a of metal. The electrodes 1a, 1b are fixed to a gauge support 1D of an insulating material, and signal wires 1c extend respectively from the electrodes 1a, 1b through a bore 1F in the gauge support 1D out of the latter.

A temperature sensor 60 for detecting the temperature of lubricating oil extends through the center of the gauge support 1D and is fixed thereto, with a signal wire 60a extending from the temperature sensor 60 through a bore 1F in the gauge support 1D out of the latter. As shown in FIG. 21(a), the outer electrode 1a has holes 1G defined at suitable positions therein for allowing passage of lubricating oil easily into a space between the inner electrode 1b and the outer electrode 1a.

Where the electrodes comprise parallel plates or cylindrical members, they should preferably be placed in an area in which the lubricating oil runs at all times, for example, at an outlet of an oil cleaner for engine oil, or be arranged normally to the surface of the lubricating oil in an oil pan, so that no foreign matter will be deposited between the electrodes.

The temperature sensor for detecting the temperature of the lubricating oil may be of a unitized construction integral with the electrodes, or may be arranged separately from the electrodes. Instead of the temperature sensor, an output from a water temperature sensor generally used in automobiles may be utilized for the same operation and advantages as described above.

In the measurement of the level and performance of the lubricating oil according to the fifteenth embodiment, the peak value at any desired position of the transient response current flowing through the lubricating oil between the electrodes when a pulse voltage is applied to the electrodes, the variation of the current in the fixed period of time, and the ratio of the peak value and the current variation may be measured separately, and may be used individually or in combination for measuring the performance of the lubricating oil.

A sixteenth embodiment (belonging to the seventh aspect) of the present invention will be described.

In a method of and an apparatus according to the sixteenth embodiment of the present invention, a pulse voltage is applied by a power supply means to at least a pair of electrodes placed in contacting relation to a dielectric fluidic substance to be measured, and a transient response current flowing bewteen the electrodes dependent on the component of the dielectric fluidic substance disposed between the electrodes is measured to evaluate the performance of the dielectric fluidic substance based on the measured current. At least one of the electrodes is made of a material having high activity to the dielectric fluidic substance, so that when a pulse voltage is applied across the dielectric fluidic substance, charged particles produced upon dissociation or electrolytic dissociation of the dielectric fluidic substance will be allowed to react with the electrode for measuring the transient response current with high sensitivity.

As described above with respect to the basic principles of the present invention, an increase in the peak value ip of the transient response current appears to be caused by the fact that the lubricating oil such as engine oil has metal particulate and residual carbon increasingly contained therein during its process of use, resulting in a progressively higher conductivity. A reduction in the current variation $\Delta i$ appears to be caused by the fact that the variation in the conductivity of engine oil becomes gradually smaller under the influence of water content and insolubles.

Therefore, for lubricating oil such as engine oil, the greater the current value ip and the smaller the current variation $\Delta i$, the lower the perfomance of the lubricating oil.

The current value ip dependent on the conductivity of the dielectric substance is divided by the current variation $\Delta i$ dependent on the size of foreign matter to determine their ratio. Since the ratio increases in proportion to the period in which the oil is used (running distance), the ratio is an effective means for evaluating the performance of a dielectric fluidic substance such as engine oil.

It has been found from numerous experimental analyses made by the inventor based on the basic principles of the invention that the difference or variation $\Delta i$ in the transient response current is largely dependent on an ionic current generated by electrolytic dissociation of an additive (a detergent-dispersant, for example, in engine oil) in the lubricating oil while a pulse voltage is being applied across the lubricating oil.

More specifically, salt of alkali earth metals contained in a detergent-dispersant serving as an additive in new oil is electrolytically dissociated when the pulse voltage is impressed, thereby producing basic ions to increase the variation $\Delta i$ in the transient response current. However, with used oil, the base in the additive is reduced due to the deterioration and contamination of the oil, and so are ions produced by electrolytic dissociation, resulting in an reduced variation $\Delta i$ in the transient response current. The above fact becomes evident if the electrodes are made of a highly active material.

FIGS. 22 through 25 are illustrative of i and $\Delta i$ of a transient response current flowing through new oil for different electrode materials (palladium, copper, brass, and stainless steel). The currents shown in FIGS. 22 through 25 can be obtained from the output from the gate means 43 and the output from the differential operation means 41 in the processing circuit means 4 according to the embodiment shown in FIG. 8. (The current graduations on the ordinate remain the same throughout FIGS. 22 through 25.) As illustrated in FIGS. 22 through 25, the electrode material which is more active to oil causes a greater variation $\Delta i$ in the transient response current.

This is considered to be caused for the following reason: The detergent-dispersant as an additive in oil is composed of salt of alkali earth metals that are organic acids and has an oxidizing catalytic action. When a pulse voltage is applied to the electrodes, therefore, the base primarily in the detergent-dispersant in the oil is electrolytically dissociated into ions, which will react with the active electrodes. This increases the variation $\Delta i$ in the transient response current, which is detected definitely. As a result of the foregoing experimental analyses, it is found that in transient response characteristics of lubricating oil which form the basis of the principles of the invention, the peak value ip at any desired position of the transient response current flowing through the lubricating oil, the current variation $\Delta i$ in a fixed period of time, and the ratio ip/$\Delta i$ are effective in grasping in general an increase in the conductivity, an increase in large foreign matter particles, and a variation in electrolytically dissociated ions due to deterioration of lubricating oil. Utilizing these parameters, a high-performance apparatus for measuring any deterioration of the essential performance of lubricating oil can be achieved.

Based on the foregoing basic principles and numerous experimental facts, the essential performance of a dielectric substance such as lubricating oil can be deteremined directly, highly accurately, reliably, and simply by placing a pair of electrodes in the dielectric fluidic substance, applying a pulse voltage to the electrodes, and measuring a peak value of a transient response current flowing between the electrodes, a variation in the current in a fixed period of time, or ratio of the peak value to the variation, while the pulse voltage is being applied to the electrodes.

Figure 26:
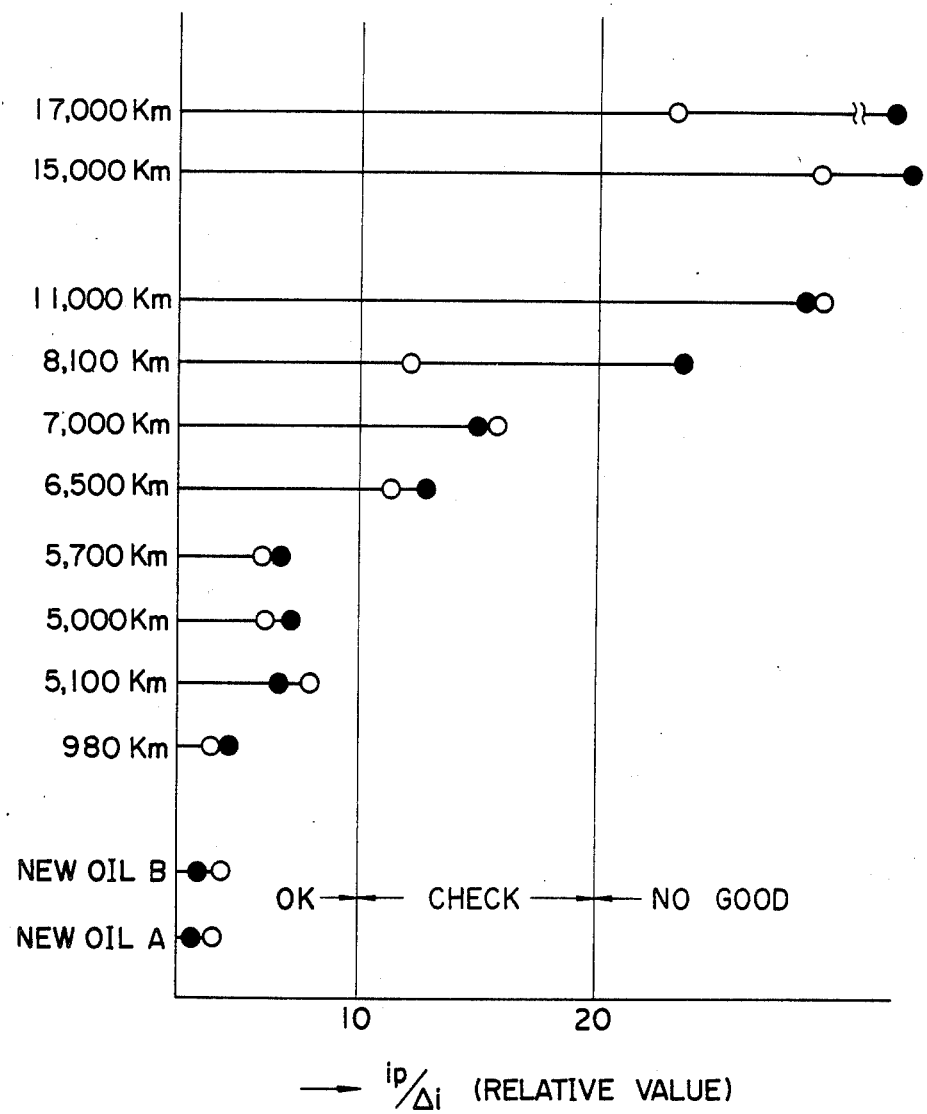
FIG. 26 is a diagram showing the results of measurement in a sixteenth embodiment.

The method of evaluating the performance of a dielectic fluidic substance according to the sixteenth embodiment was applied to engine oil in an automobile, using the evaluation apparatus according to the fifth embodiment (FIG. 8), and the results are shown in FIG. 26.

Designated in FIG. 26 at white circles are results obtained with electrodes made of brass, and black circles are results obtained with electrodes made of copper plated with palladium.

It can be seen from FIG. 26 that the electrodes plated with palladium having a greater catalytic action on oil can determine the performance of oil with higher accuracy. This is because the variation $\Delta i$ in the transient response current is largely dependent on electrolytically dissociated basic ions contained in an additive in the oil.

Where the apparatus for measuring the performance of lubricating oil according to the sixteenth embodiment is incorporated in an automobile, it is preferable that the electrodes be made of cobalt, palladium, or platinum singly, or copper, nickel, or iron plated with a catalytic material such as palladium or platinum for increased durability and corrosion resistance.

By constructing at least one of the electrodes of a material having a catalytic action, it is possible to detect an increased variation $\Delta i$ in the transient response current, so that the apparatus for measuring the performance of lubricating oil will have an increased accuracy and sensitivity. With a positive electrode being made of an catalytic material, ions generated by electrolytic dissociation of an additive in lubricating oil can be detected highly efficiently, thus increasing a variation $\Delta i$ in the transient response current.

Where the electrodes are placed in contact with lubricating oil for a short period of time for measuring the performance of the lubricating oil (such as in a gasoline station or a repair shop), it is possible construct the electrodes directly of copper.

An apparatus for evaluating the performance of a dielectric fluidic substance according to a seventeenth embodiment (belonging to the second aspect) of the present invention will be described, the apparatus being suitable for use in an automobile repair shop or a service station.

The apparatus for evaluating the performance of a dielectric fluidic substance according to the seventeenth embodiment comprises a measuring container accommodating lubricating oil to be measured and having at least a pair of electrodes held in contact with the lubricating oil, a power supply means for applying a pulse voltage of a fixed amplitude and a fixed time duration to the electrodes, a current detecting means for detecting a current flowing between the electrodes due to a transient response of the lubricating oil between the electrodes when the pulse voltage is applied, a processing circuit means for computing a ratio of a peak value at a desired position of the current to a variation in the current in a fixed period of time after the desired position, and a display means for displaying an output from processing circuit means as the degree (performance) to which the lubricating oil is deteriorated. The measuring container comprises a receptacle body having an accommodating portion accommodating a prescribed amount of the lubricating oil and an openable and closable member which is openable and closable with respect to the receptacle body. The accommodating portion and the openable and closable member have portions confronting each other and supporting the pair of electrodes in confronting relation with a prescribed distance therebetween, the electrodes serving to sandwich a prescribed thickness of the lubricating oil therebetween. The electrodes have cables for connection to an external measuring apparatus. The apparatus according to this embodiment has a reservoir in the confronting portions of the accommodating portion and the openable and closable member. The reservoir communicates with a given gap defined by the pair of electrodes and serves to allow the electrodes to sandwich the prescribed thickness of the lubricating oil. Furthermore, at least one of the confronting portions of the accommodating portion and the openable and closable member has an ultrasonic vibrator disposed therein for stirring and mixing the lubricating oil to be measured or cleaning the lubricating oil attached to the electrodes.

According to this apparatus, the electrodes can freely be opened and closed for effecting measurements quickly and simply. In particular, the electrode surfaces can easily be cleaned in each cycle of measurement. Stirring and mixing of the lubricating oil due to ultrasonic vibration or ultrasonic cleaning can improve a measuring accuracy and clean small dirt particles off the electrode surfaces highly effectively.

Since the electrodes are provided in pair according to the seventeenth embodiment, it is possible to greatly reduce the quantity of lubricating oil to be measured. For example, the apparatus of the present invention can effect measurement on an amount of 0.5 to 1 cc of engine oil attached to the distal end of an oil level gauge mounted in an engine oil pan for the purpose of measuring the level of the engine oil. Accordingly, the performance of lubricating oil can be measured with utmost ease and in easy operation. Because the measuring container according to the present embodiment is quite simple in construction, the apparatus can be maintained easily and manufactured less costly.

Figure 27:
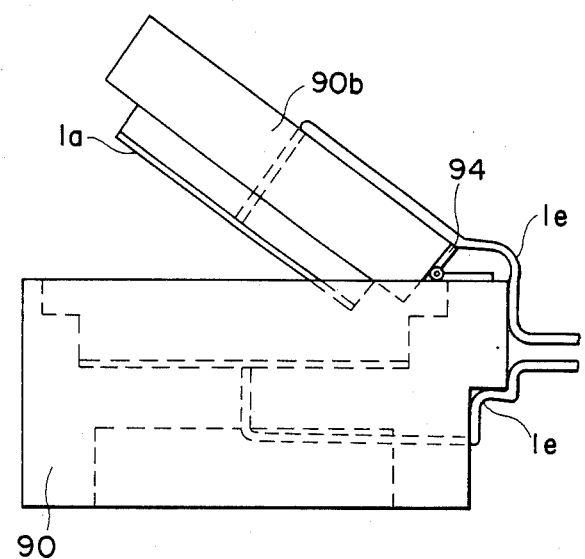
FIG. 27 is a side elevational view of a container, as it is open, of an apparatus of an eighteenth embodiment.
Figure 28:
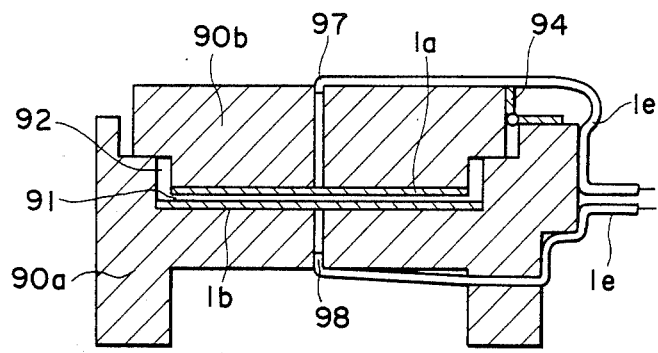
FIG. 28 is a cross-sectional view of the container shown in FIG. 27.

FIGS. 27 and 28 show a measuring container in an apparatus for measuring the performance of lubricating oil according to an eighteenth embodiment (belonging to the second aspect) of the present invention. FIG. 27 is a side elevational view of the measuring container as it is open, and FIG. 28 is a cross-sectional view of the measuring container.

The measuring container, designated at 90, is made of an insulating material such as a resin material. The measuring container 90 is composed of a receptacle 90a, an electrode plate 1b disposed in a lubricating oil accommodating portion 91 in the receptacle 90a, a cable 1e extending from the electrode 1b through an outlet 98 in the receptacle 90a for connection to an external measuring apparatus, an electrode plate 1a disposed in confronting relation to the electrode plate 1b and spaced a distance from the electrode plate 1b, a cover 90b serving as an openable and closable member supporting the electrode plate 1a and made of an insulating material, a cable 1e extending from the electrode 1a through an outlet 97 in the cover 90b for connection to the external measuring apparatus, a hinge 94 for allowing the cover 90b to be opened and closed with respect to the receptacle 90a, and a reservoir 92 for storing excessive oil from the accommodating portion 91.

In operation, lubricating oil or the like to be measured is put into the accommodating portion 91 in the receptacle 90, and then sandwiched between the electrode plates 1a, 1b. A pulse voltage is applied to the electrode plate 1a by the external measuring apparatus through the cable 1e. A transient response current flowing at this time through the lubricating oil between the electrode plates 1a, 1b is measured through the cable 1e by the external measuring apparatus and evaluated for grasping the performance of the lubricating oil with utmost ease.

With the measuring container 90 thus constructed and operated, the electrode plate 1a is freely openable and closable by the hinge 94 with respect to the receptacle 90a.

According to the eighteenth embodiment, any oil attached to the electrodes 1a, 1b or remaining in the accommodating portion 91 and the reservoir 92 in a previous cycle of measurement can easily be cleaned away prior to use of the measuring container 90 for a next cycle of measurement.

More specifically, the cover 90b of the container 90 is opened, oil attached to the electrodes 1a, 1b is wiped off, and the electrodes 1a, 1b are then cleansed by a solvent such as hexane. Therefore, any residual oil from the previous measurement can be washed off simply. The cleaning of the container 90 is important since if oil other than lubricating oil to be measured were attached to the electrode plates and other members upon measurement of the performance of the lubricating oil, the accuracy of the performance of the lubricating oil would largely be affected. The measuring container 90 according to the present embodiment is therefore highly advantageous in that the measuring container 90 can easily be cleaned, the accuracy of measurement of the performance of the lubricating oil remains stable, and the measuring container 90 can easily be handled.

The gap between the electrodes 1a, 1b, that is, the gap in which the lubricating oil to be measured is sandwiched, is quite small, so that the necessary amount of lubricating oil to be measured can be reduced to a large extent. For example, each of the electrode plates 1a, 1b is composed of a circular plate of brass which is 40 mm across, and the gap between the electrodes is 1 mm. The quantity of oil sandwiched between the electrodes 1a, 1b is about 1.2 cc. This quantity of oil can be picked up easily by an oil level gauge which is mounted in an engine for measuring the remaining amount of engine oil in the engine. Accordingly, the measuring container 90 can serve as a simple means for measuring the performance of engine oil in an automobile repair shop or a gasoline station.

The reservoir 92 in the receptacle 90 allows the user to confirm the amount of lubricating oil to be put in the accommodating portion 91 and prevents any excessive oil from overflowing the container 90. More specifically, when lubricating oil to be measured in the accommodating portion 91 is present in the reservoir 92, it can easily be confirmed that the gap between the electrode plates 1a, 1b is filled with the lubricating oil. The easy confirmation of the amount of lubricating oil to be measured is advantageous in that if no sufficient amount of lubricating oil were filled between the electrode plates 1a, 1b and if air were present between the electrode plates 1a, 1b, the accuracy of measurement of the performance of the lubricating oil would be influenced. The reservoir 92 is also effective in preventing lubricating oil to be measured from overflowing the measuring container 90 when an excessive amount of lubricating oil is introduced into the container 90.

The reservoir 92 may be defined through the cover 90b so that any excessive oil will be forced upwardly.

The electrode plates 1a, 1b may be rectangular in shape, rather than circular.

While the receptacle 90a and the cover 90b have been described as being made of an insulating material, they may be made of other materials provided that they allow the electrode plates 1a, 1b to be disposed in confronting relation with a constant gap provided therebetween. For example, the cover 90b and the electrode plate 1a may be of a unitary construction made of an electrically conductive material.

The receptacle 90 may be made of a transparent material such as acrylic resin so that the amount of oil present in the accommodating portion 91 can be visually checked through the side wall of the receptacle 90.

Figure 29:
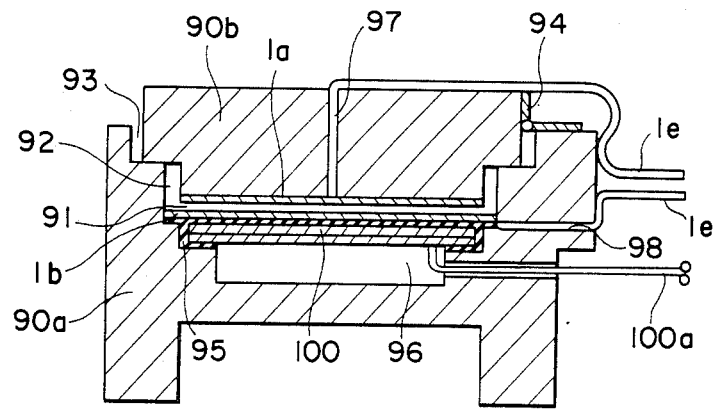
FIG. 29 is a cross-sectional view of a container of an apparatus of a nineteenth embodiment.

FIG. 29 shows a measuring container 90 according to a nineteenth embodiment (belonging to the second aspect) of the present invention. Structurally and functionally identical parts shown in FIG. 29 are denoted by identical reference characters in FIGS. 27 and 28, and will not be described in detail.

FIG. 29 is a cross-sectional view of the measuring container according to the nineteenth embodiment. The measuring container 90 is composed of a receptacle 90a made of an insulating material such as a resin material, an electrode plate 1b disposed in a lubricating oil accommodating portion 91 in the receptacle 90a, a cable 1e extending from the electrode plate 1b through an outlet 98 in the receptacle 90a for connection to an external measuring apparatus, an ultrasonic vibrator 100 placed on a support 95 below the electrode plate 1b, an acoustic space 96 below the ultrasonic vibrator 100, a signal cable 100a extending from the ultrasonic vibrator 100, an electrode plate 1a disposed in confronting relation to the electrode plate 1b and spaced a distance from the electrode plate 1b, a cover 90b supporting the electrode plate 1a and made of an insulating material, a cable 1e extending from the electrode 1a through an outlet 97 in the cover 90b for connection to the external measuring apparatus, a hinge 94 for allowing the cover 90b to be opened and closed with respect to the receptacle 90a, and a reservoir 92 for storing excessive oil from the accommodating portion 91.

In operation, for cleaning the measuring container 90, oil attached to the electrode plates 1a, 1b is wiped off, and then a solvent such as gasoline or hexane is put into the accommodating portion 91 in the container 90. Thereafter, a power supply in the external measuring apparatus for generating an ultrasonic signal is actuated to apply an ultrasonic signal via the signal cable 100a to the ultrasonic vibrator 100 for vibrating the latter to effect ultrasonic cleaning. Therefore, any dirt such as oil attached to the electrode plates 1a, 1b and the accommodating portion 91 can effectively be cleaned away in a short period of time by the ultrasonic cleaning mechanism to keep the interior of the measuring container 90 in a clean condition. This is advantageous in that the accuracy of measurement of the performance of lubricating oil remains stable and the measuring container 90 can easily be maintained.

The ultrasonic vibrator 100 may be positioned anywhere provided it can clean the surfaces of the accommodating portion 91 and the electrode plates 1a, 1b. The acoustic space 96 for the ultrasonic vibrator 100 may not be hollow, but may be of any other construction for transmitting an acoustic output from the ultrasonic vibrator 100 efficiently to the electrode plate 1b. The ultrasonic vibrator 100 can apply an ultrasonic energy to the layer of lubricating oil sandwiched between the electrodes immediately prior to measuring operation for thereby stirring and mixing the lubricating oil to increase the subsequent measuring accuracy.

Figure 30:
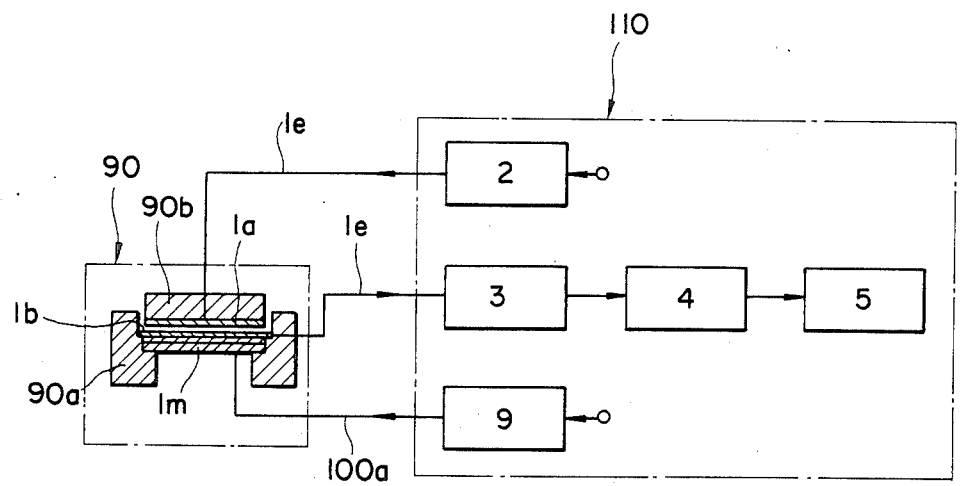
FIG. 30 is a block diagram of a twentieth embodiment with a measuring container, shown in cross-section.

An apparatus for measuring the performance of lubricating oil, using a measuring container 90, according to a twentieth embodiment of the present invention will be described with reference to FIG. 30. The measuring apparatus comprises a measuring container 90 and an apparatus section 110. The apparatus section 110 comprises a power supply means 2 for applying a pulse voltage of a fixed amplitude and a fixed time duration through a cable 1c to an electrode plate 1a disposed on a cover 90b of the measuring container 90, a current detecting means 3 for measuring a current flowing from an electrode plate 1b in a receptacle 90a through a cable 1e due to a transient response of lubricating oil disposed between the electrode plates 1a, 1b while the pulse voltage is being applied by the power supply means 2 to the electrode plate 1a, a processing circuit means 4 for detecting a peak value at a desired position of the transient reponse current through the lubricating oil detected by the current detecting means 3 and a variation in the current in a fixed period of time after the desired position, and for computing a ratio of the peak value to the current variation, a display means 5 for displaying an output from the processing circuit means as the performance value of the lubricating oil, and an ultrasonic power supply means 9 for supplying an ultrasonic signal through a signal cable 100a to an ultrasonic vibrator 100 disposed in the measuring container 90 when the latter is to be cleaned.

In operation, when the performance of lubricating oil or the like is to be measured, the lubricating oil to be measured is put into the measuring container 90, and sandwiched between the electrode plates 1a, 1b. The power supply means 2 is then actuated by a measuring starting command to apply a pulse voltage to the electrode plate 1a.

A transient response current flowing dependent on the performance of the lubricating oil between the electrode plates 1a, 1b when the pulse voltage is applied is passed through the electrode 1b and the cable 1e and measured by the current detecting means 3. The transient response current varies with the performance, conductivity, or condition of electrolytic dissociation of the lubricating oil, and serves as an index indicative of the performance (the degree to which the lubricating oil is deteriorated) of the lubricating oil according the principles of the invention as described above.

The processing circuit means 4 computes a ratio of a peak value at any desired position of the transient response current to a variation of the current in a fixed period of time after the desired position, and the ratio is displayed as the performance value of the lubricating oil by the display means 5.

After the performance of the lubricating oil has been measured, the lubricating oil in the measuring container 90 is wiped off by a piece of cloth or paper, and then a solvent such as gasoline or hexane is put into the measuring container. The ultrasonic power supply 9 is now energized to actuate the ultrasonic vibrator in the container 90 to ultrasonically clean the interior of the measuring container 90.

Therefore, the measuring container for use in an apparatus for measuring the performance of lubricating oil such as engine oil in an automobile repair shop or a gasoline station has a pair of electrodes spaced a gap from each other, with one of the electrodes being mounted on a cover openable and closable with respect to the container.

This construction has the following advantages:

(1) The measuring container (including the electrodes) can easily be cleaned, and the measuring apparatus can easily be operated and maintained.

(2) With the pair of electrodes used, the measuring container is quite simple in construction, can be operated with ease, is highly durable, and can be constructed inexpensively.

By placing the ultrasonic vibrator in the container for ultrasonic cleaning of the container, the following advantages result:

(3) The measuring container can be cleaned effectively, in a short period of time, and with ease.

(4) Small dirt particles on the electrode surfaces can effectively be cleaned off, the measuring container and the measuring apparatus are highly reliable in operation, and the desired accuracy of measurement of the performance can be maintained.

An apparatus according to a twenty-first embodiment for warning the deterioration of engine oil or the like can grasp an increase of an electrically conductive substance which is responsive for engine oil deterioration by applying a pulse voltage to a pair of electrodes held in contact with engine oil for an automobile, for example, and measuring transient response characteristics of the engine oil.

The apparatus for warning the deterioration of engine oil, comprises a sensor means having at least a pair of electrodes held in contact with engine oil to be measured and a temperature sensor for detecting the temperature of the engine oil, a temperature detecting means responsive to an output from the temperature sensor for determining that the engine oil is in a prescribed temperature range, a timing circuit means energizable by an output signal from the temperature detecting means and a signal indicative of actuation of an engine starting switch for issuing a measuring signal to measure the condition of deterioration of the engine oil, a power supply means energizable by an output from the timing circuit means for generating and applying a pulse voltage having a fixed amplitude and a fixed time duration to the electrodes in the sensor means, a current detecting means for detecting a transient response current flowing through the engine oil between the electrodes when the pulse voltage is applied by the power supply means to the electrodes in the sensor means, a processing circuit means for detecting a peak value at a desired position of the transient reponse current and a variation in the current in a fixed period of time, and for computing a ratio of the peak value to the current variation, a discriminating circuit means for comparing the peak value and the ratio from the processing circuit means with a preset discrimination reference value, and for issuing a discriminated result indicative of a condition of deterioration of the engine oil, and a display means for displaying the condition of deterioration of the engine oil dependent on the output from the discriminating circuit means.

The warning apparatus thus constructed can accurately measure the property, the degree of contamination, and the service life of engine oil itself for an automobile, for example, and hence can consribute to the society from the standpoint of saving natural resources such as oil. Where the warning apparatus is installed on an automobile, the driver can know the condition of engine oil, with the results that the automobile performance can be improved, and safety and fuel economy of the automobile can also be increased.

An apparatus for warning the deterioration of engine oil according to a twenty-second embodiment of the present invention will be described with reference to FIGS. 31 through 34

The apparatus has a sensor means 1 composed of at least a pair of electrodes disposed in an oil pan in an engine in contact with engine oil and a temperature sensor for detecting the temperature of the engine oil.

The apparatus also comprises a cable means 12 connecting the sensor means 1 and a warning device II placed on the instrument panel in an automobile, for example. The warning device II has a temperature detecting means 6 for converting an output signal from the temperature sensor in the sensor means 1 and generating a measurement command signal when the oil temperature is in a prescribed temperature range, and a timing circuit means 11 responsive to an output from the temperature detecting means 6 and a signal from an engine starting switch for generating a timing signal to control measurement. The warning device II further includes a power supply means 2 for applying a pulse voltage of a fixed amplitude and a fixed time duration to the electrodes in the sensor means 1, and a current detecting means 3 for detecting a transient response current flowing due to a transient response of the oil between the electrodes when the pulse voltage is applied to the electrodes in the sensor means 1. The warning device II also includes a processing circuit means 4 for detecting a peak value at a desired position of an output from the current detecting means 3, a variation in the current in a fixed period of time, and a ratio of the peak value to the current variation, a discriminating circuit means 10 for comparing an output from the processing circuit means 4 with a reference value, and a display means 5 responsive to an output from the discriminating circuit means 10 for displaying the condition of deterioration of the engine oil for the driver.

The components of the apparatus shown in FIG. 31 and their operation will be described in greater detail with reference to FIGS. 32, 33 and 34.

Figure 32A:
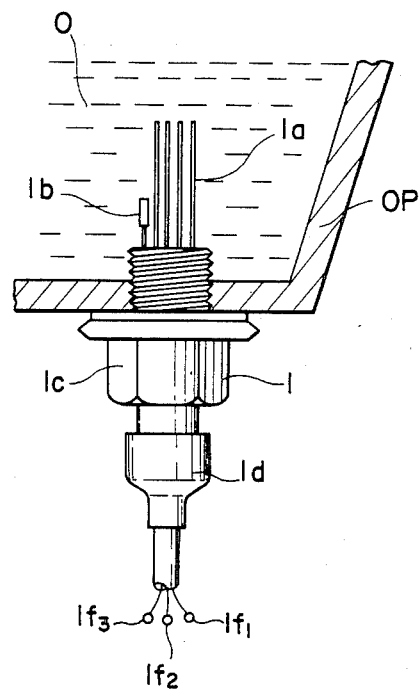
Figures 32B, 32C:
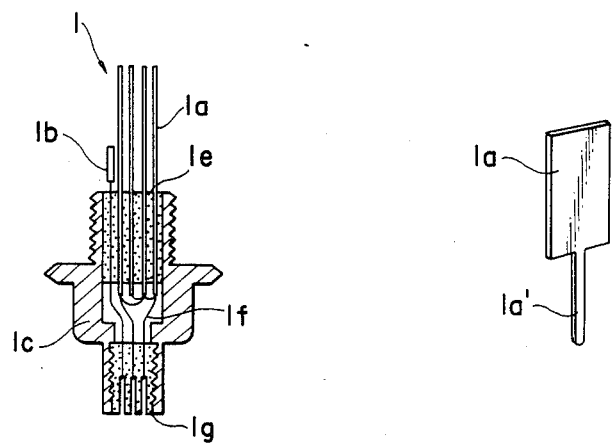
Figure 33:
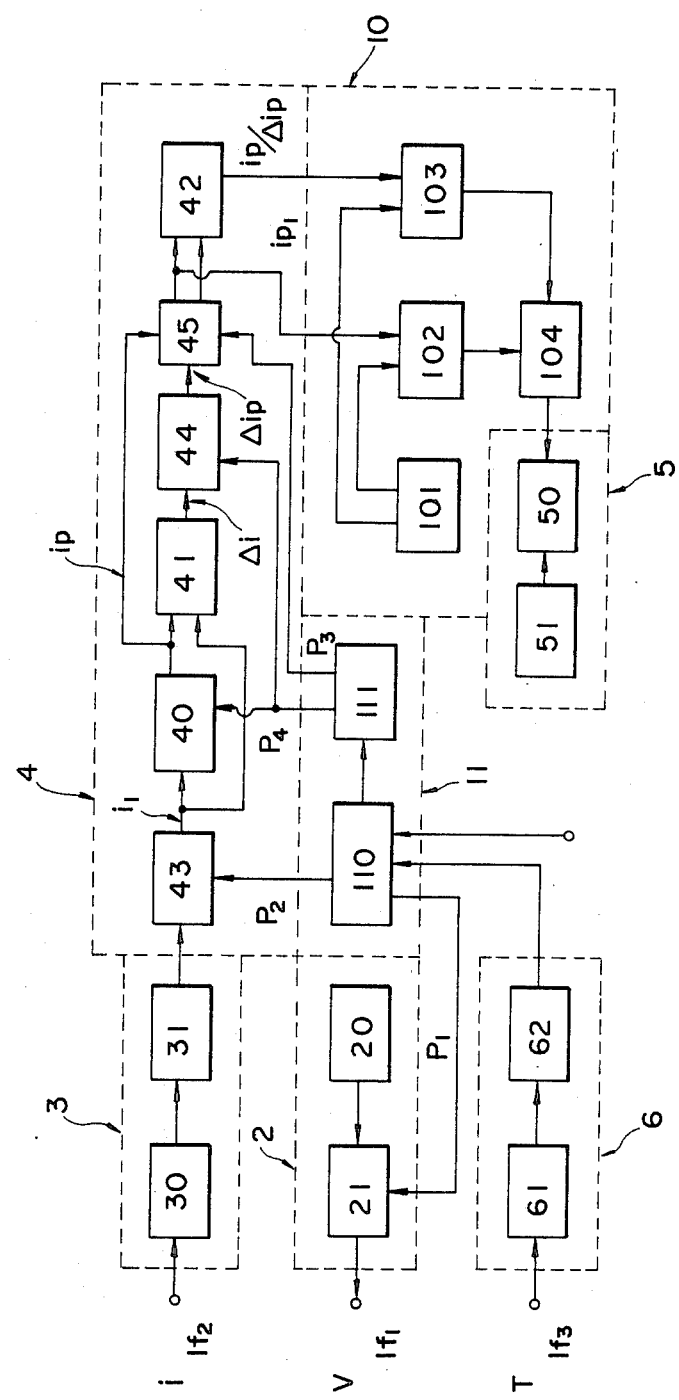

FIGS. 32(a), 32(b) and 32(c) show a preferred construction of the sensor means 1 in the warning apparatus according to this embodiment.

As shown in FIG. 32(a), the sensor means 1 comprises a support 1c, at least a pair of electrodes 1a mounted on the support 1c in electrically insulating relation, a temperature sensor 1b, and a connector 1d connecting the electrodes 1a and the temperature sensor 1b to the warning device II. The sensor means 1 is attached to an oil pan OP in an engine with the electrodes 1a and the temperature sensor 1b disposed in oil O.

FIG. 32(b) shows the sensor means 1 in cross section, and FIG. 32(c) illustrates one of the electrodes 1a.

The electrodes 1a and the temperature sensor 1b are embedded in an insulating block 1e (as of ceramic) fixedly mounted in the support 1c. As shown in FIG. 32(c), each of the electrodes 1a is flat and has a connector 1a' extending from a lower end of the electrode 1a. The connectors 1a' are electrically connected by lead wires 1f to a coupling 1g for connection to an external connector 1d, from which lead wires $1f_1$, $1f_2$ extend. Likewise, the temperature sensor 1b has a lead wire embedded in the insulating block 1e and connected to the coupling 1g, from which a lead wire $1f_3$ extends.

The sensor means 1 may be mounted as a drain plug on the engine oil pan OP so that the sensor means can be detached and attached for oil replacement. The sensor means 1 will be detached when an oil replacement is indicated by the warning apparatus, and when detached, the electrodes 1a can be cleaned. The sensor means 1 can therefore be easily maintained, and will have a required degree of reliability and durability.

The warning device II will be described in detail with reference to FIGS. 33 and 34. The temperature sensor 1b in the sensor means 1 is connected by the lead wire $1f_3$ to the temperature detecting means 6. The temperature detecting means 6 comprises a temperature detecting circuit 61 for converting an output from the temperature sernsor 1b into a temperature signal, and a discriminating circuit 62 for generating a measurement command signal when the engine oil is in a prescribed temperature range. With this arrangement, a command signal for measuring the degree of deterioration of engine oil can be generated when the temperature of the engine oil is raised to a prescribed temperature on warning-up of the engine, no matter what initial conditions of the engine may be, that is, no matter what temperature the ambient air and the engine oil may have during cold or warm seasons.

The prescribed temperature of the engine oil means a temperature range in which the performance of the engine oil can be measured at maximum sensitivity with high reliability based on the princples of the invention. For engine oil for automobiles, the temperature range has been experimetally detertmined to be from 5° C. to 70° C. In such temperature range, the optimum oil temperature is approximately normal temperature.

The measurement command signal from the temperature detecting means 6 is fed to the timing circuit means 11. The timing circuit means 11 comprises a timing circuit 110 and a reset circuit 111 and is energized by the measurement command signal and a signal from the engine starting swtich.

With this arrangement, when the engine starting switch is turned on or the engine is started, a signal is issued to actuate a power supply (not shown) to set the warning device II in operation.

When the engine oil to be measured is determined by the temperature detecting means 6 to be in the prescribed temperature range during such operation mode, the timing circuit 110 issues a signal $P_1$ (FIG. 34(a)) having a fixed time duration $T_0$ for energizing the power supply means 2.

With a time delay equal to a fixed time duration $T_1$ after the signal $P_1$, the timing circuit 110 issues a signal $P_2$ (FIG. 34(b)) having a fixed time duration $T_2$ for energizing the processing circuit means 4.

After the output or the signal $P_2$ has been issued from the timing circuit 110, the reset circuit 111 issues a signal $P_3$ (FIG. 34(c)) having a fixed time duration $T_3$ and a signal $P_4$ (FIG. 34(d)) to the processing circuit means 4.

The power supply means 2 includes a power supply 20 for generating a constant DC voltage and a switching circuit 21 for converting an output from the power supply 20 into a pulse voltage. The power supply means 2 can produce a pulse voltage having a fixed amplitude V and a fixed time duration $T_0$, and the pulse voltage V (FIG. 34(e)) is applied through the lead wire $1f_1$ to one of the electrodes 1a in the sensor means 1.

The current detecting means 3 is connected by the lead wire $1f_2$ to the other electrode 1a. The current detecting means 3 comprises a current detecting circuit 30 for detecting a transient response current flowing between the electrodes 1a due to a transient response of the engine oil between the electrodes 1a when a pulse voltage is applied by the power suply means 2 across the engine oil, and a low-pass filter 31. The current detecting means 3 thus constructed can convert the transient response current of a high impedance flowing through the engine oil between the electrodes 1a into a voltage signal of a low impedance, and remove noise contained in the transient response current, with the results that a correct transient response current i (FIG. 34(f)) can be detected.

In response to signals from the current detecting means 3 and the timing circuit means 11, the processing cirucit means 4 processes the transient response current. The processing circuit means 4 comprises a first gate 43 energizable by an output signal $P_2$ from the timing circuit 110, a peak detecting circuit 40 for measuring a peak value ip of a current signal $i_1$ (FIG. 34(g)) having a fixed time duration $T_2$ at a desired position of the transient response current i detected by the gate 43, a differential operation circuit 41 supplied with an output ip (FIG. 34(h)) from the peak detecting circuit 40 and the current signal $i_1$ for measuring a currentvariation $\Delta i$ (FIG. 34(i)) in the time duration $T_2$, a holding circuit 44 for holding the maximum value $\Delta ip$ (FIG. 34(j)) of the output $\Delta i$ from the differential operation circuit 41, a second gate 45 for passing the output ip from the peak detecting circuit 40 and the output ip from the holding circuit 44 during a period of time in which the pulse signal $P_3$ (FIG. 34(c)) having the time duration $T_3$ issued from the reset circuit is being applied, and a division circuit 42 for computing a ratio $\Delta ip/ip$ (FIG. 34(l)) of a singal $ip_1$ (FIG. 34(k)) corresponding to the peak value ip from the gate 45 to the signal $\Delta ip$ (FIG. 34(j)) corresponding to the current variation $\Delta i$.

Operation of the first gate 60 is as follows:

It is assumed that the pulse voltage generated by the power supply means 2 has a time duration $T_0$ and a voltage value V. When the pulse voltage (FIG. 34(e)) is applied to the electrode in the sensor means 1, a transient response current i (FIG. 34(f)) flows through the engine oil between the electrodes. The peak detecting circuit 40 in the processing circuit means 4 has an ability to detect a peak value ip (FIG. 34(g)) of the transient response current after the time period $T_1$ due to the gate 43, after the pulse voltage of the time duration $T_0$ has been applied to the electrode 1a. The transient response current ip detected by the peak detecting circuit 40 is fed to one of input terminals of the differential operation circuit 41, which the transient response current upon elapse of the time duration $T_1$ is fed to the other input terminal of the differential operation circuit 41. The differential operation circuit 41 computes the difference between the input signals to detect the variation $\Delta i$ (FIG. 34(i)) of the transient response current in the time period $T_2$.

The discriminating circuit means 10 is supplied with the signal $ip_1$ corresponding to the peak value at any desired position of the transient response current through the engine oil measured by the processing circuit means 4, and the signal $ip/\Delta i$ indicating the ratio of the peak value to the current variation $\Delta i$ in the time period.

The discriminating circuit means 10 comprises a reference circuit 101 for setting different reference values for different types of engine oil, a first discriminating circuit 102 for comparing the peak value signal $ip_1$ with the reference value for discrimination, a second discriminating circuit 103 for comparing the ratio signal $ip/\Delta i$ with the reference value, and a discriminating circuit 104 responsive to outputs from the first and second discriminating circuits for determining display of the degree of deterioration of the engine oil.

The reference circuit 101 may be arranged to select and set initial performance values of engine oil dependent on the types thereof (for gasoline engines and diesel engines, for instance) and properties (due to different viscosities and additives). The differentiating circuit means 10 then can determine the degree of deterioration of engine oil accurately while the engine oil is in the process of being used. Since reference values of oil can freely be set at the time a different oil is used upon oil replacement, the differentiating circuit means 10 can be used in a wide range of applications for different oil types.

The first discriminating circuit 102 serves to determine the degree of deterioration of oil due to electrically conductive materials such as metal particulates and sludge contained in the engine oil, based on the magnitude of the peak value ip. The second discriminating circuit 103 serves to determine the degree of deterioration of oil due to the correlation between the electrically conductive materials and the size of foreign matter particles such as of water and insolubles, based on the magnitude of the ratio $ip/\Delta i$.

The discriminating circuit 104 has an ability for selecting outputs from the first and second discriminating circuits, and can discriminate oil deterioration due to an increase in the electrically conductive materials in the oil, oil deterioration due to an increase in the dielectric fluidic substance in the oil, or oil deterioration due to the correlation between the preceding two types of deterioration.

The display means 5 is composed of a display unit 50 such as lamps or a buzzer for indicating the degree of deterioration of oil for the driver in response to an output from the discriminating circuit means 10, and a backup mechanism 51 for holding an NG display until the oil is replaced.

In the warning device II thus constructed, the power supply 20 in the power supply means 2 may be arranged to have an inverter for converting a voltage from a battery on an automobile or a primary voltage signal generated by an igniter on a gasoline engine into a DC voltage.

The display means 5 may be arranged to display not only the performance value or service life of the lubricating oil at the time it is measured, but also a remaining life of the lubricating oil or a remaining travel distance by holding an initial performance value of the lubricating oil at the time it is not used in the reference circuit 101 and comparing the determined performance value with the initial performance value, if the property and type of the lubricating oil to be measured is known.

The sensor means 1 has been shown as being mounted on the engine oil pan, and may be positioned anywhere in the engine oil pan provided it is held in contact with engine oil.

The sensor means 1 may be disposed in a pipe connected to the outlet of an engine oil cleaner so that sludge contained in engine oil will be prevented from entering the sensor means 1 towards the electrodes 1a.

The sensor means 1, particularly the electrodes 1a, may be disposed normally to the surface level of engine oil for preventing foreign matter in engine oil from being deposited between the electrodes 1a.

The electrodes 1a in the sensor means 1 may be covered entirely with a mesh for preventing sludge from finding its way in between the electrodes.

The temperature sensor 16 in the sensor means 1 may be dispensed with, an an output from a water temperature installed on an automobile engine may be utilized The apparatus for warning the deterioration of engine oil may be used with not only engine oil but also transmission oil.

A portion of the circuit of the warning device and the discriminating process may be shared and implemented by a computer equipped in an engine control system, for example.

Although certain preferred embodiments have been shown and described, it should be understood that many changes and modifications may be made therein without departing from the scope of the appended claims

What is claimed is:

1. A method of evaluating the quality of a dielectric fluidic substance, comprising the steps of:
   applying a pulsed voltage to at least a pair of electrodes arranged so as to be in contact with said dielectric fluidic substance, wherein said pulsed voltage has a fixed amplitude and fixed time duration;
   detecting the transient response current flowing between said electrodes depending upon the quality of the dielectric fluidic substance disposed between said electrodes when said pulsed voltage is applied,
   detecting and processing the transient response current to extrapolate a steady-state current over a fixed period of time;
   measuring and comparing with a predetermined reference value at least one of a peak value of said extrapolated steady-state current, a difference between the peak value and a value at a fixed period of time after the peak value has been detected and a ratio of the peak value so detected and the difference between the peak value and a value at a fixed period of time after the peak value has been detected; and
   displaying the value of the measured and compared value.

2. A method according to claim 1, further comprising the step of detecting a temperature of the dielectric substance, said pulse voltage being applied to the electrodes when the temperature of the dielectric substance is equal to a prescribed temperature.

3. A method according to claim 2, further comprising the step of controlling the temperature of the dielectric substance to a prescribed temperature.

4. A method according to claim 1, further comprising the step of detecting a temperature of the dielectric substance, said pulse voltage being applied to the electrodes when the temperature of the dielectric substance is equal to a prescribed temperature, wherein
   the peak value is displayed as a value indicative of a liquid level of the dielectric substance and the ratio of the peak value to the difference between the two values is displayed as a value indicative of the quality of the dielectric substance.

5. A method according to claim 1, wherein at least one of said electrodes is made of a material having a relatively large catalytic activity with respect to the dielectric substance.

6. An apparatus for evaluating the quality of a dielectric fluidic substance, comprising:
   at least a pair of electrodes disposed in contact with the dielectric substance to be measured;
   power supply mans for applying a pulse voltage having a fixed value and a fixed amplitude to said electrodes;
   timing circuit means for energizing said power supply when measuring conditions of the dielectric substance are met;
   current detecting means including a load resistor and a low-pass filter for detecting a transient response current flowing between said electrodes dependent on the dielectric substance disposed between said electrodes;
   signal processing means including a gate circuit for detecting a steady-state current in the transient response current upon elapse of a certain period of time from an initial value of said transient response current and within a fixed period of time;
   a computing circuit for computing a peak value of the steady-state current from said gate circuit, a difference between the peak value and a value at a fixed period of time after the peak value, and a ratio of the peak value to the difference between and two values; and
   display means comprising means for displaying an output from said signal processing means and discriminating circuit means for setting a reference value dependent on the quality of the dielectric substance and for comparing the output from said computing circuit with said reference value to determine the quality of the dielectirc substance.

7. An apparatus according to claim 6, further including temperature detecting means for detecting the temperature of the dielectric substance, said pulse voltage being applied by said power supply means when the dielectric substance is at a prescribed temperature.

8. An apparatus according to claim 7, wherein said temperature detecting means comprises a temperature detecting element, including sensor means of a unitary construction composed of said temperature detecting element and said electrodes in electrically insulated relation, said sensor means being removably locatable in the dielectric substance.

9. An apparatus according to claim 6, further comprising a measuring container for the dielectric substance made of an insulating material in which said electrodes are disposed and lead wires extending from said electrodes, temperature detecting means disposed in said measuring container for detecting the temperature of the dielectric substance, and temperature controlling means for heating or cooling the dielectric substance in said measuring container to a prescribed temperature.

10. An apparatus according to claim 6, further comprising an oil level gauge for an automobile, said electrodes being mounted on a tip of said oil level gauge in an electrically insulated relation thereto, and lead wires extending from said electrodes on said oil level gauge.

11. An apparatus according to claim 6, wherein said display means comprises means for setting the peak value of the current from said signal processing means as a value indicative of a liquid level of the dielectric substance, setting one of the peak value, the difference between the two values and the ratio from said signal processing means as a value indicative of the quality of the dielectric substance, correcting said peak value with said ratio, and measuring and displaying the liquid level of the dielectric substance based on the corrected peak value.

12. An apparatus according to claim 6, wherein at least one of said electrodes is made of a material highly active with respect to the dielectric substance and selected from the group consisting of platinum, palladium, copper, iron, nickel, and brass.

13. An apparatus according to claim 6 further comprising a measuring container for the dielectric substance made of an insulating material in which said electrodes are disposed and lead wires extending from said electrodes, said measuring container comprising a receptacle having an accommodating portion for accommodating a prescribed amount of dielectric substance, a member openable and closable with respect to said receptacle, said receptacle and said openable and closable member having confronting portions on which said electrodes are supported, respectively, in spaced relation, for sandwiching a layer of the dielectric substance in a gap therebetween and a reservoir defined between said confronting portions for storing the dielectric substance and providing the same to said gap, said openable and closable member having a through hole for permitting an excessive amount of dielectric substance to flow upwardly.

14. An apparatus for evaluating the quality of a dielectric fluidic substance comprising:
   sensor means having at least a pair of electrodes held in contact with engine oil to be measured and a temperature sensor for detecting the temperature of the engine oil;
   temperature detecting means responsive to an output from said temperature sensor for determining that the engine oil is in a prescribed temperature range;
   timing circuit means energizable by an output signal from said temperature detecting means and a signal indicative of actuation of an engine starting switch;
   power supply means energizable by an output from said timing circuit means for generating and applying a pulse voltage having a fixed amplitude and a fixed time duration to said electrodes in said sensor means;
   current detecting means for detecting a transient response current flowing through the engine oil between said electrodes when the pulse voltage is applied by said power supply means to said electrodes in said sensor means;
   signal processing means for detecting at least one of a peak value of a steady-state current in the transient response current within a fixed period of time, a difference between the peak value and a value at a fixed period of time after the peak value, and for computing a ratio of the peak value to the difference between the two values; and
   display means comprising discriminating circuit means for comparing at least one of the peak value, the difference between the two values and the ratio from said processing circuit means with respective preset discrimination reference values, and for issuing a discriminated result indicative of a condition of deterioration of the engine oil; and means for displaying the condition of deterioration of the engine oil dependent on the output from said discriminating circuit means.

15. An apparatus for evaluating the plurality of a dielectric fluidic substance, comprising:
   at least a pair of electrodes disposed in contact with the dielectric fluidic substance to be measured;
   power supply means for applying a pulse voltage having a fixed amplitude and a fixed time duration to said electrodes;
   current detecting means for detecting a transient response current flowing between said electrodes depending on the quality of the dielectric fluidic substance disposed between said electrodes; and
   signal processing means connected to said current detecting means, for processing the detected transient response current to extrapolate a steady-state current with a fixed period of time and for measuring at least one of the peak value of said steady-current, a difference between a peak value and a value at a fixed period of time after the measurement of said peak value and a ratio of the peak value and a difference between the peak value and a value at a fixed period of time after the measurement of said peak value; and
   display means connected to said signal processing means, for displaying the obtained value and comparing the value with a reference value indicative of the quality of the dielectric substance.

16. An apparatus according to claim 15 further comprising sensor means connected to said power supply means and said current detecting means, wherein said sensor means has a support of an insulating material to which said electrodes are fixed and lead wires are extended from said electrodes, said sensor means being removably inserted into the dielectric fluidic substance.

17. An apparatus according to claim 16, further comprising a measuring container made of an insulating material and connected to said power supply means and said current detecting means, in which said dielectric fluidic substance is sandwiched between said electrodes, lead wires being extended from said electrodes.

18. An apparatus according to claim 17, wherein said measuring container comprises a receptacle having an accommodating portion for accommodating a prescribed amount of dielectric substance to be measured, and a member openable and closable with respect to said receptacle, said receptacle and said openable and closable member having confronting portions on which said electrodes are supported, respectively, in spaced relation, for sandwiching a layer of the dielectric substance in a gap therebetween, and lead wires extending from said electrodes, respectively, for connection to said power supply means and said current detecting means.

19. An apparatus according to claim 18, wherein said measuring container further comprises a reservoir defined between said confronting portions for storing the dielectric substance and providing the same to said gap.

20. An apparatus according to claim 19, wherein said openable and closable member has a through hole for permitting an excessive amount of dielectric substance to flow upwardly.

21. An apparatus according to claim 17, wherein said measuring container further comprises an ultrasonic vibrator for mixing the dielectric substance and removing deposits of dielectric substance from said electrodes.

22. An apparatus according to claim 15, wherein said signal processing means comprises peak detecting means for detecting a peak value of the steady-state current.

23. An apparatus according to claim 15, wherein said signal processing means comprises peak detecting means connected to said current detecting means, for detecting a peak value of the steady-state current, and differential operation means connected to said current detecting means and said peak detecting means, for detecting a difference between the peak value and a value at a fixed period of time after the peak value.

24. An apparatus according to claim 15, wherein said signal processing means comprises peak detecting means connected to said current detecting means, for detecting a peak value of the steady-state current, differential operation means connected to said current detecting means and said peak detecting means, for detecting a difference between the peak value and a value at a fixed period of time after the peak value, and division means connected to said peak detecting means and said differential operation means, for measuring the ratio of the peak value to the difference between the two values.

25. An apparatus according to claim 15, wherein said signal processing means comprises gate means connected to said power supply means and said current detecting means, for measuring the steady-state current upon elapse of a certain period of time from a initial value of the transient response current.

26. An apparatus according to claim 15, further comprising temperature detecting means connected to said power supply means, for detecting a temperature of the dielectric substance, said pulse voltage being applied by said power supply means when the dielectric substance is at a prescribed temperature.

27. An apparatus according to claim 26, wherein said display means further comprises discriminating means for comparing at least one of the peak value, the difference between the two values and the ratio of the peak value to the difference between the two values with the reference value.

28. An apparatus according to claim 27, wherein said discriminating means comprises a memory for setting the reference value indicative of the initial quality of the dielectric substance dependent on the type and quality of the dielectric substance.

29. An apparatus according to claim 28, wherein said discriminating means comprises a discriminating circuit for alotting the reference value to measured values issued from said signal processing means and selectively discriminating the measured values according to the present priority.

30. An apparatus according to claim 26 wherein said display means comprises means for displaying the peak value of the current as a value indicative of a liquid level of the dielectric substance and the ratio of the peak value to the difference between the two values as a value indicative of the quality of the dielectric substance.

31. An apparatus according to claim 26, further comprising temperature controlling means connected to said temperature detecting means, for controlling the temperature of the dielectric substance to a prescribed temperature.

32. An apparatus according to claim 26, further comprising timing circuit means connected to said power supply means, responsive to an output from said temperature detecting means for energizing said power supply means to generate the pulse voltage when the dielectric substance is at the prescribed temperature.

33. An apparatus according to claim 26, wherein said temperature detecting means and said electrodes are of unitary construction in electrically insulated relation.

34. An apparatus according to claim 26, wherein said displaying means comprises means for converting the peak value into an area of contact between said electrodes and the dielectric substance and for displaying said area as a liquid level of the dielectric substance.

35. An apparatus according to claim 34, wherein said displaying means comprising means for measuring a reduction of a peak value of the steady-state current at the time of measurement from a reference peak value of the steady-state current, for converting said reduction into a liquid level of the dielectric substance, and displaying said liquid level.

36. An apparatus according to claim 35 wherein said displaying means comprises means for correcting the reduction of the peak value with the ratio of the peak value to the difference between the two values.

37. An apparatus according to claim 15, wherein at least one of said electrodes is made of a material having a catalytic activity with respect to the dielectric substance.

38. An apparatus according to claim 15, wherein said current detecting means comprises a load resistor and a low-pass filter for removing noise signals from the transient response current.

39. An apparatus according to claim 37, wherein a positive electrode of said electrodes has the catalytic activity.

40. An apparatus according to claim 37, wherein said material is selected from the group consisting of platinum, palladium, copper, iron, nickel and brass.

41. An apparatus according to claim 15, wherein said electrodes comprise a cylindrical electrode assembly including a body of insulating material, a first electrode mounted centrally on said body, and a second cylindrical electrode surrounding said first electrode with a gap therebetween in an electrically insulated relation to said first electrode, said second electrode having through holes for passage of the dielectric substance to be measured.

42. An apparatus according to claim 15 wherein said display means further comprises discriminating means for comparing at least one of the peak value, the difference between the two values and the ratio of the peak value to the difference between the values with the reference value.

* * * * *

UNITED STATES PATENT AND TRADEMARK OFFICE
CERTIFICATE OF CORRECTION

PATENT NO. :    4,686,857
DATED       :   August 18, 1987
INVENTOR(S) :   Takayuki Kato It is certified that error appears in the above-identified patent and that said Letters Patent is hereby corrected as shown below:

Number of drawings printed incorrectly on Letters Patent. Should read as follows:

- 42 Claims, 60 Drawing Figures -

Signed and Sealed this

Nineteenth Day of January, 1988

*Attest:*

DONALD J. QUIGG

*Attesting Officer*   *Commissioner of Patents and Trademarks*